(12) United States Patent
Lv et al.

(10) Patent No.: US 11,713,357 B2
(45) Date of Patent: Aug. 1, 2023

(54) CD38 PROTEIN ANTIBODY AND APPLICATION THEREOF

(71) Applicants: HANGZHOU SUMGEN BIOTECH CO., LTD., Zhejiang (CN); SUMGEN MAB (BEIJING) BIOTECH CO., LTD., Beijing (CN)

(72) Inventors: Ming Lv, Zhejiang (CN); Xiaoran Ding, Zhejiang (CN); Shiwei Miao, Zhejiang (CN); Bin Tan, Zhejiang (CN); Xuegong Wang, Zhejiang (CN)

(73) Assignees: HANGZHOU SUMGEN BIOTECH CO., LTD., Zhejiang (CN); SUMGEN MAB (BEIJING) BIOTECH CO., LTD., Beijing (CN)

(*) Notice: Subject to any disclaimer, the term of this patent is extended or adjusted under 35 U.S.C. 154(b) by 104 days.

(21) Appl. No.: 16/968,994

(22) PCT Filed: Feb. 11, 2019

(86) PCT No.: PCT/CN2019/074806
§ 371 (c)(1),
(2) Date: Aug. 11, 2020

(87) PCT Pub. No.: WO2019/154421
PCT Pub. Date: Aug. 15, 2019

(65) Prior Publication Data
US 2021/0024645 A1  Jan. 28, 2021

(30) Foreign Application Priority Data
Feb. 12, 2018 (CN) .......................... 201810144817.4

(51) Int. Cl.
*C07K 16/00* (2006.01)
*C07K 16/28* (2006.01)
*A61P 35/00* (2006.01)
*A61P 35/02* (2006.01)
*C12N 5/10* (2006.01)
*A61K 48/00* (2006.01)
*A61K 31/713* (2006.01)
*C12N 15/63* (2006.01)
*A61K 39/00* (2006.01)

(52) U.S. Cl.
CPC ........ *C07K 16/2896* (2013.01); *A61K 31/713* (2013.01); *A61K 48/00* (2013.01); *A61P 35/00* (2018.01); *A61P 35/02* (2018.01); *C12N 5/10* (2013.01); *C12N 15/63* (2013.01); *A61K 2039/505* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/732* (2013.01); *C07K 2317/76* (2013.01); *C07K 2317/92* (2013.01)

(58) Field of Classification Search
CPC ............ C07K 16/2896; C07K 2317/24; C07K 2317/515; C07K 2317/56; C07K 2317/565; C07K 2317/732; C07K 2317/92; A61K 48/00; A61K 2039/505; A61P 35/00
See application file for complete search history.

(56) References Cited

U.S. PATENT DOCUMENTS

2017/0121414 A1* 5/2017 Jansson .................. A61P 35/00

FOREIGN PATENT DOCUMENTS

| CN | 101218256 A | 7/2008 |
|---|---|---|
| CN | 101616933 A | 12/2009 |
| CN | 103282383 A | 9/2013 |
| IN | 4718/CHENP/2007 A | 11/2008 |
| JP | 2015110597 A | 6/2015 |
| MX | 2009004050 A | 4/2009 |
| RU | 2402568 C2 | 10/2010 |
| WO | 2006099875 A1 | 9/2006 |
| WO | 2007042309 A2 | 4/2007 |
| WO | WO2010040209 * | 4/2010 |
| WO | 2012092612 A1 | 7/2012 |
| WO | 2016180958 A1 | 11/2016 |
| WO | 2016187546 A1 | 11/2016 |
| WO | 2018224682 A1 | 12/2018 |
| WO | WO2018/224683 * | 12/2018 |

OTHER PUBLICATIONS

Hebbes, Tim R., et al., A "Minimal Epitope" Anti-Protein Antibody That Recognises A Single Modified Amino Acid, Molecular Immunology, vol. 26, No. 9, pp. 865-876, 1989, Pergamon Press PLC.
Niels, W.C.J. van de Donk, et al., Monoclonal antibodies targeting CD38 in hematological malignancies and beyond, Immunological Reviews, 270, pp. 95-112, 2016, John Wiley & Songs Ltd.
Royt, A., et al., Immunology, Chapter 6, pp. 110-111, 2000.
Royt, A., et al., Immunology, Chapter 9, p. 150, 2000.
Singer, Maxine, et al., Genes & Genomes, A Changing Perspective, The Genetic Molecules, pp. 63-64 (68-69), 1991, University Science Books.
Sundberg, Eric J., Structural Basis of Antibody-Antigen Interactions, Methods in Molecular Biology, epitope Mapping Protocols, vol. 524, Chapter 2, pp. 23-36, 2009, Humana Press.

(Continued)

*Primary Examiner* — Lei Yao
(74) *Attorney, Agent, or Firm* — Honigman LLP; Thomas A. Wootton, Esq.; Jonathan P. O'Brien

(57) ABSTRACT

Provided by the invention is an antibody or an antigen-binding fragment thereof, which binds to a CD38 protein at a $K_D$ value below $1\times10^{-9}$M. The antibody or an antigen-binding fragment thereof has strong specific recognition and binding capabilities for CD38 protein, and may kill CD38+ cells by means of antibody-dependent cell-mediated cytotoxicity (ADCC), complement-dependent cytotoxicity (CDC) and/or apoptosis. Further provided by the present invention is an application of the antibody or antigen-binding fragment thereof in preventing and treating tumors.

7 Claims, 10 Drawing Sheets
Specification includes a Sequence Listing.

(56) References Cited

OTHER PUBLICATIONS

EP 19751277.5 Extended European Search Report dated Nov. 9, 2021.
Deckert, Jutta, et al., SAR650984, A Novel Humanized CD38-Targeting Antibody, Demonstrates Potent Antitumor Activity in Models of Multiple Myeloma and Other CD38 Hematologic Malignancies, Clinical Cancer Research, 10(17) Sep. 1, 2014, American Association for Cancer Research.
Smithson, Glennda, et al., TAK-079 is a high affinity monoclonal antibody that effectively mediates CD38+ cell depletion, The Journal of immunology, vol. 198, Issue 1 Supplement 224.20, May 1, 2017.
PCT/CN2019/074806 International Search Report dated May 24, 2019.

\* cited by examiner

CD38 PROTEIN ANTIBODY AND APPLICATION THEREOF

CROSS-REFERENCE TO RELATED APPLICATIONS

This application is a National Stage Application and claims priority under 35 U.S.C. § 371 to Patent Cooperation Treaty application PCT/CN2019/074806, filed Feb. 11, 2019, which claims the benefit of CN 201810144817.4, filed Feb. 12, 2018. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "8-11-2020_262790-471488_Seq_Listing_ST25.txt" is 39,198 bytes in size and was created on Aug. 11, 2020, and filed electronically herewith.

TECHNICAL FIELD

The present application relates to the biomedical field, in particular to an antibody capable of binding to the CD38 protein.

BACKGROUND ART

CD38 protein is a bifunctional exonuclease which can catalyze the conversion of NAD$^+$ to cyclic ADP-ribose (cADPR, cyclic ADP-ribose) and hydrolyze cADPR to ADP ribose. CD38 protein is one of the antigens expressed on malignant plasmacytes, and expressed in various malignant hematopoietic cells, comprising but not limited to multiple myeloma cells, B cell chronic lymphoblastic leukemia cells, and B cell acute lymphatic cell type leukemia cells.

However, the currently developed CD38 antibodies have limited recognition activity, limited cytotoxic activity, and limited ability in inhibiting tumors, therefore there is an urgent need to develop a new CD38 antibody for development of new drugs.

SUMMARY OF THE INVENTION

The present application provides a CD38 antibody and an application thereof. The CD38 antibody provided in the present application may comprise one or more of the following properties: 1) it may bind to the CD38 protein with a higher affinity and specificity; 2) it may kill CD38$^+$ cells by means of antibody-dependent cell-mediated cytotoxicity (ADCC), complement-dependent cytotoxicity (CDC) and/or apoptosis; 3) it may kill and damage tumor cells and/or inhibit tumor growth; 4) it may be used for preventing or treating tumors; 5) it may inhibit the binding of a CD38 protein to CD38 ligand. The present application further provides a preparation method and application of the CD38 antibody.

On the one hand, the present application provides an antibody or an antigen-binding fragment thereof, which binds to a CD38 protein at a $K_D$ value of $1\times10^{-9}$M or below.

In some embodiments, the antibody or an antigen-binding fragment thereof in the present application can kill and damage tumor cells and/or inhibit tumor growth by specifically binding to CD38 protein.

In some embodiments, the antibody or the antigen-binding fragment thereof in the present application can kill CD38$^+$ cells by means of antibody-dependent cell-mediated cytotoxicity (ADCC), complement-dependent cytotoxicity (CDC) and/or apoptosis.

In some embodiments, the antibody or the antigen-binding fragment thereof in the present application does not bind or substantially does not bind to BSA, CD19, TROP2, CD47, AXL or Gas6 and other unrelated antigens.

In some embodiments, the tumors comprise a CD38 positive tumor. In some embodiments, the CD38 positive tumor is selected from the group comprising multiple myeloma, lymphoma and leukemia.

In some embodiments, the tumor is selected from the group comprising non-Hodgkin lymphoma and Hodgkin's lymphoma.

In some embodiments, the tumor cell comprises those selected from the group comprising Raji cell, Daudi cell, Ramos cell and RPMI8226 cell.

In some embodiments, the antibody or the antigen-binding fragment thereof binds to one or more residues corresponding to amino acid residues 60-89 of human CD38 protein when binding to the CD38 protein (wherein the amino acid sequence of amino acids 60-89 of the human CD38 protein is as shown in SEQ ID NO:15).

In some embodiments, the antibody is selected from the group comprising monoclonal antibody, single-strand antibody, chimeric antibody, humanized antibody and fully human antibody.

In some embodiments, the antigen-binding fragment is selected from the group comprising Fab, Fab', F(ab)2, F(ab')2, Fv and ScFv.

In some embodiments, the CD38 protein is human CD38 protein or monkey CD38 protein. For example, the CD38 protein may not be mouse CD38 protein, or may not be rat CD38 protein.

In some embodiments, the antibody or an antigen-binding fragment thereof according to the present application competes with a reference antibody to bind to the CD38 protein, wherein the reference antibody comprises a light chain variable region and a heavy chain variable region, the light chain variable region of the reference antibody comprises LCDR1, LCDR2 and LCDR3, the LCDR1 comprises an amino acid sequence as shown in SEQ ID NO:1; the LCDR2 comprises an amino acid sequence as shown in SEQ ID NO:2; the LCDR3 comprises an amino acid sequence as shown in SEQ ID NO:3, the heavy chain variable region of the reference antibody comprises HCDR1, HCDR2 and HCDR3, the HCDR1 comprises an amino acid sequence as shown in SEQ ID NO:4; the HCDR2 comprises an amino acid sequence as shown in SEQ ID NO:5; and the HCDR3 comprises an amino acid sequence as shown in SEQ ID NO:6.

In some embodiments, the light chain variable region of the reference antibody comprises an amino acid sequence as shown in SEQ ID NO:7, and the heavy chain variable region of the reference antibody comprises an amino acid sequence as shown in SEQ ID NO:8.

In some embodiments, the light chain of the reference antibody comprises an amino acid sequence as shown in SEQ ID NO:22. For example, the light chain of the reference antibody or the fragment thereof comprises an amino acid sequence as shown in any one of SEQ ID NO:11, SEQ ID NO:16, SEQ ID NO:18 and SEQ ID NO:20.

In some embodiments, the heavy chain of the reference antibody comprises an amino acid sequence as shown in SEQ ID NO:23. For example, the heavy chain of the reference antibody or the fragment thereof comprises an amino acid sequence as shown in any one of SEQ ID NO:13, SEQ ID NO:17, SEQ ID NO:19 and SEQ ID NO:21.

In some embodiments, the antibody or the antigen-binding fragment thereof in the present application comprises the light chain of an antibody or a fragment thereof. In some embodiments, the light chain of the antibody or the fragment thereof comprises LCDR1, and the LCDR1 comprises an amino acid sequence as shown in SEQ ID NO:1. In some embodiments, the light chain of the antibody or the fragment thereof comprises LCDR2, and the LCDR2 comprises an amino acid sequence as shown in SEQ ID NO:2. In some embodiments, the light chain of the antibody or the fragment thereof comprises LCDR3, and the LCDR3 comprises an amino acid sequence as shown in SEQ ID NO:3.

In some embodiments, the light chain of the antibody or the fragment thereof comprises a light chain variable region VL, and the light chain variable region VL comprises an amino acid sequence as shown in SEQ ID NO:7.

In some embodiments, the light chain of the antibody or the fragment thereof further comprises a human constant region. In some embodiments, the human constant region comprises a human Igκ constant region.

In some embodiments, the light chain of the antibody or the fragment thereof comprises an amino acid sequence as shown in SEQ ID NO:22. For example, the light chain of the antibody or the fragment thereof comprises an amino acid sequence as shown in any one of SEQ ID NO:11, SEQ ID NO:16, SEQ ID NO:18 and SEQ ID NO:20.

In some embodiments, the antibody or an antigen-binding fragment thereof comprises a heavy chain of an antibody or a fragment thereof. In some embodiments, the heavy chain of the antibody or the fragment thereof comprises HCDR1, and the HCDR1 comprises an amino acid sequence as shown in SEQ ID NO:4. In some embodiments, the heavy chain of the antibody or the fragment thereof comprises HCDR2, and the HCDR2 comprises an amino acid sequence as shown in SEQ ID NO:5. In some embodiments, the heavy chain of the antibody or the fragment thereof comprises HCDR3, and the HCDR3 comprises an amino acid sequence as shown in SEQ ID NO:6.

In some embodiments, the heavy chain of the antibody or the fragment thereof comprises a heavy chain variable region VH, and the heavy chain variable region VH comprises an amino acid sequence as shown in SEQ ID NO:8.

In some embodiments, the heavy chain of the antibody or the fragment thereof further comprises a human constant region. In some embodiments, the human constant region comprises a human IgG constant region. In some embodiments, the IgG constant region comprises a human IgG1 constant region.

In some embodiments, the heavy chain of the antibody comprises an amino acid sequence as shown in SEQ ID NO:23. For example, the heavy chain of the antibody or the fragment thereof comprises an amino acid sequence as shown in any one of SEQ ID NO:13, SEQ ID NO:17, SEQ ID NO:19 and SEQ ID NO:21.

On the other hand, the present application provides an isolated nucleic acid molecule which comprises a polynucleotide encoding an antibody or an antigen-binding fragment thereof in the present application.

In some embodiments, at least one of the nucleic acid molecules is codon optimized.

In some embodiments, the nucleic acid molecule comprises one or more polynucleotide sequences selected from the group comprising SEQ ID NO:9, SEQ ID NO:10, SEQ ID NO:12 and SEQ ID NO:14.

On the other hand, the present application provides a vector, which comprises the nucleic acid molecule in the present application.

On the other hand, the present application provides a cell, which comprises the nucleic acid molecule in the present application or the vector in the present application.

On the other hand, the present application provides a method for preparing an antibody or an antigen-binding fragment thereof. The method comprises culturing the cell in the present application under conditions which allow the expression of the antibody or the antigen-binding fragment thereof.

On the other hand, the present application provides a pharmaceutical composition, which comprises the antibody or the antigen-binding fragment thereof, the nucleic acid molecule, the vector and/or the cell in the present application, and optionally pharmaceutically acceptable adjuvants.

On the other hand, the present application provides an application of the antibody or an antigen-binding fragment thereof in preparation of medicaments for preventing or treating tumors.

In some embodiments, the tumors comprise a CD38 positive tumor. In some embodiments, the CD38 positive tumor is selected from the group comprising multiple myeloma, lymphoma and leukemia. In some embodiments, the tumor is selected from the group comprising non-Hodgkin lymphoma and Hodgkin's lymphoma.

On the other hand, the antibody or the antigen-binding fragment thereof provided in the present application may be used for preventing or treating tumors.

In some embodiments, the tumors comprise a CD38 positive tumor. In some embodiments, the CD38 positive tumor is selected from the group comprising multiple myeloma, lymphoma and leukemia. In some embodiments, the tumor is selected from the group comprising non-Hodgkin lymphoma and Hodgkin's lymphoma.

On the other hand, the present application provides a method for preventing or treating tumors. The method comprises administering to a subject in need the antibody or the antigen-binding fragment thereof, the molecular nucleic acid, the vector, the cell and/or the pharmaceutical composition in the present application.

In some embodiments, the tumors comprise a CD38 positive tumor. In some embodiments, the CD38 positive tumor is selected from the group comprising multiple myeloma, lymphoma and leukemia. In some embodiments, the tumor is selected from the group comprising non-Hodgkin lymphoma and Hodgkin's lymphoma.

On the other hand, the present application provides a method for inhibiting the binding of a CD38 protein to a CD38 ligand, and the method comprises administering the antibody or the antigen-binding fragment thereof, the nucleic acid molecule, the vector and/or the cell in the present application.

In some embodiments, the CD38 ligand comprises CD31.

Additional aspects and advantages of the present disclosure will become readily apparent to those skilled in this art from the following detailed description, wherein only illustrative embodiments of the present disclosure are shown and described. Numerous modifications of the embodiments of the disclosure described herein will now occur to those skilled in the art without departing from the disclosure.

BRIEF DESCRIPTION OF THE DRAWINGS

Specific features of the invention as set forth in this application are set forth in the appended claims. The features and advantages of the inventions of the present application can be better understood by referring to the exemplary embodiments and the accompanying drawings. A brief description of the drawing is as follows:

DETAILED DESCRIPTION OF THE EMBODIMENTS

Figure 1:
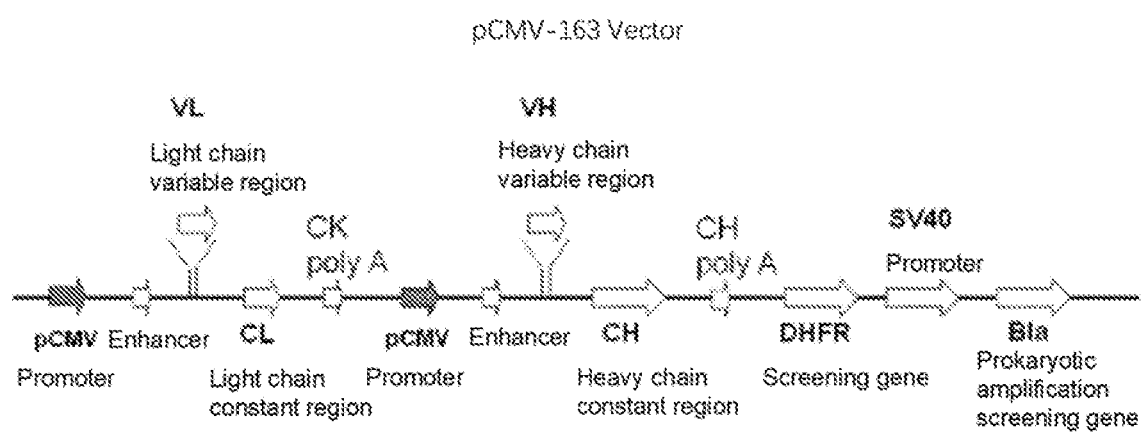
FIG. 1 shows a physical map of constructing the antibody SG003 of the present application into a whole antibody expression vector.

The embodiments of the present invention are described below by way of specific embodiments, and those skilled in the art can readily appreciate other advantages and effects of the present invention from the disclosure of the present specification.

In the present application, the term "antibody" refers usually to a peptide capable of specifically recognizing and/or neutralizing a specific antigen. For example, the antibody may comprise an immunoglobulin composed of at least two heavy (H) chains and two light (L) chains linked to each other by disulfide bonds, and may comprise any molecule comprising an antigen-binding fragment thereof. The term "antibody" comprises a monoclonal antibody, a fragment of an antibody or an antibody derivative, comprising but not limited to, human antibody (fully human antibody), humanized antibody, chimeric antibody, single-strand antibody (e.g., scFv), and an antigen-binding fragment of the antibody (e.g., Fab, Fab' and (Fab)$_2$ fragment). The term "antibody" further comprises all the recombinant forms of the antibody, such as, an antibody expressed in a prokaryotic cell, nonglycosylated antibody and any antigen-binding fragment of the antibody of the present application and a derivative thereof. Each heavy chain may be composed of a heavy chain variable region (VH) and a heavy chain constant region. Each light chain may be composed of a light chain variable region (VL) and a light chain constant region. The VH and VL regions may be further divided into hypervariable regions (known as complementary determining regions (CDRs)), which are dispersed between more conserved regions known as framework regions (FRs). Each VH and VL may be composed of three CDRs and four FRs, which may be arranged from the amino terminal to the carboxy terminal in an order of FR1, CDR1, FR2, CDR2, FR3, CDR3 and FR4. The variable regions of the heavy chain and the light chain contain binding domains that interact with the antigen. The constant regions of the antibody may mediate the binding of the immunoglobulin to a host tissue or a factor, which comprises a plurality of cells (e.g., effect cells) of the immune system and the first component (Clq) of the classic complement system.

In the present application, the term "antibody-binding fragment" refers usually to one or more fragments of the antibody which serve to specifically bind to the antigen. The antigen binding function of the antibody may be implemented by the full-length fragment of the antibody. The antigen binding function of the antibody may also be implemented by the followings: a heavy chain comprising a fragment of Fv, ScFv, dsFv, Fab, Fab' or F(ab')$_2$, or a light chain comprising a fragment of Fv, ScFv, dsFv, Fab, Fab' or F(ab')$_2$. (1) Fab fragment, that is, a monovalent fragment comprising VL, VH, CL and CH domains; (2) F(ab')2 fragment, a divalent fragment comprising two Fab fragments linked by a disulfide bond in the hinge region; (3) an Fd fragment comprising VH and CH domains; (4) an Fv fragment comprising VL and VH domains in one arm of an antibody; (5) a dAb fragment comprising a VH domain (Ward et al., (1989) Nature 341: 544-546); (6) isolated complementary determining region (CDR); and (7) a combination of two or more isolated CDRs which are optionally linked by a linker. Moreover, a monovalent single-strand molecule Fv (scFv) formed by pairing of VL and VH may further be included (see Bird et al., (1988) Science 242: 423-426; and Huston et al., (1988) Proc. Natl. Acad. Sci. 85: 5879-5883). The "antigen binding moiety" may further comprise an immunoglobulin fusion protein which comprises a binding domain selected from the group comprising (1) a binding domain peptide fused with an immunoglobulin hinge region peptide; (2) an immunoglobulin heavy chain CH2 constant region fused with a hinge region; and (3) an immunoglobulin heavy chain CH3 constant region fused with a CH2 constant region.

In the present application, the terms "CD38 protein" and "CD38 antigen" are interchangeably used herein, and comprise any variant, isotype, and species homolog of CD38, which are naturally expressed in cells or expressed in cells transfected with a CD38 gene. In the present application, the CD38 may be a human CD38 with an accession number in GenBank of BAA18966.1. In the present application, the CD38 may be a monkey CD38, such as, Macaque CD38 with an accession number in GenBank of AAT36330.1. The CD38 protein of the present application may also be known as ADP ribosyl cyclase 1, cADPr hydrolase 1, Cd38-rs1, cyclic ADP-ribose hydrolase 1, 1-19 or NIM-R5 antigen. A "CD38$^+$ cell" refers usually to a cell that expresses the CD38 protein. It may also be known as a CD38 positive cell. A "CD38$^-$ cell" refers usually to a cell that does not substantially express the CD38 protein.

In the present application, the term "CD31 protein" refers usually to a 130-140 kDa transmembrane glycoprotein found on the surface of platelets, at the joint of cultured endothelial cells, and in myeloid cell lines, and is also known as platelet endothelial cell adhesion molecule-1 (PECAM-1/CD31). In the present application, the CD31 may be a human CD31 with an accession number in GenBank of NP_000433.4. The CD31 may be used as a ligand for CD38 to play a role in thrombosis and angiogenesis.

In the present application, the term "ADCC" is antibody-dependent cell-mediated cytotoxicity (ADCC), and usually means that a cell with killing activity recognizes the Fc segment coated on the target antigen through the Fc receptor (FcR) expressed on its surface. With the aid of ADCC, the effector cells of the immune system actively dissolve the target cells whose membrane surface antigens have been bound by specific antibodies.

In the present application, the term "CDC" is complement-dependent cytotoxicity (CDC), and refers usually to a cytotoxic effect in which a complement involves. That is, the specific antibody binds to the corresponding antigen on the surface of the cell membrane to form a complex and activate the classic complement pathway. The formed membrane attack complex produces a lytic effect on the target cell.

In the present application, the term "cancer" usually refers to or describes a physiological status of a mammal, which may be typically characterized by dysregulation of cell proliferation or survival. Examples of cancer comprise but are not limited to carcinoma, lymphoma, blastoma, sarcoma and leukemia, as well as lymphoid malignant tumor. For example, cancer may be lymphoma.

In the present application, the term "lymphoma" refers usually to malignant tumor in lymphatic system. The occurrence of lymphoma is due to the uncontrolled proliferation of lymph node cells or lymph cells, and the generation of cancer cells with abnormal capabilities that may invade other tissues throughout the body. Lymphoma has many subtypes, wherein the two main types are Hodgkin's lymphoma and non-Hodgkin lymphoma. In the present application, the term "Hodgkin's lymphoma" (HL) refers usually to a class of lymphoma produced by lymphocytes of white blood cells. In the present application, the term "non-Hodgkin lymphoma" (NHL) refers usually to other classes of lymphoma except Hodgkin's lymphoma.

In the present application, the term "leukemia" refers usually to a malignant proliferative disease of the hematopoietic system that refers usually to a class of diseases caused by massive proliferation and accumulation of leukemia cells. Clonal leukemia cells largely proliferate and accumulate in bone marrow and other hematopoietic tissues due to uncontrolled proliferation, dysdifferentiation, and apoptosis inhibition or similar mechanisms, infiltrate other non-hematopoietic tissues and organs, and meanwhile inhibit the normal hematopoietic function. The followings may be clinically found: varying degrees of anemia, bleeding, fever with infection, as well as enlargement of liver, spleen, and lymph glands, and bone pain.

In the present application, the term "multiple myeloma" (MM) refers usually to a malignant tumor that invades the bone marrow due to abnormal proliferation of plasma cells. Multiple myeloma causes cancer cells to accumulate in the bone marrow, causing healthy blood cells to be excluded. Cancer cells produce abnormal proteins that may cause complications instead of normal antibodies.

In the present application, the term "Raji cell" refers usually to a continuous human cell line capable of producing Epstein-Barr virus strains. The virus will transform umbilical cord lymphocytes and induce early antigen in Raji cell. Raji cell is widely used as a transfection host, and also used to understand malignant tumors of hematopoietic cells and other cells. Moreover, since the Raji cell has and expresses several receptors that express certain complement components as well as Fc receptors of immunoglobulin protein G, it is also used to detect immune complexes.

In the present application, the term "Daudi cell" refers usually to a cell line derived from Burkitt lymphoma. Although the Daudi cell has an intracellular Class I heavy chain, no Class I human leukocyte antigen (HLA) molecules express on its surface. This is because its gene encoding β2-microsphere protein (β2m) is defective, so that the protein lacks a translatable mRNA.

In the present application, the term "Ramos cell" refers usually to a Burkitt lymphoma cell line. The cell does not carry the Epstein-Barr virus strain, and secretes IgM.

In the present application, the term "RPMI8226 cell" refers usually to a human multiple myeloma cell line.

In the present application, the term "$K_D$" is interchangeably used with "KD", and refers usually to the dissociation equilibrium constant for a specific antibody-antigen interaction in M (mol/L). KD may be calculated based on the concentrations of a substance AB and the substances A and B dissociated therefrom: KD=c (A)*c (B)/c (AB). It may be known from this formula that the greater the KD value, the more the dissociation, and the weaker the affinity between the substances A and B; on the contrary, the smaller the KD value, the less the dissociation, and the stronger the affinity between the substances A and B.

In the present application, the term "monoclonal antibody" refers usually to a population of substantially homologous antibodies, that is, various antibodies in this population are the same except the naturally occurring mutations that may exist in trace amounts. The monoclonal antibody is highly specific, and directly targets a single antigenic site. For example, the monoclonal antibody may be prepared by hybridoma technology or it is feasible to produce the monoclonal antibody by using a recombinant DNA method in bacteria, eukaryotes or plant cells. The monoclonal antibody may also be obtained from the phage antibody library, using a technology as described in for example Clackson et al., Nature, 352:624-628 (1991) and Marks et al., Mol. Biol., 222:581-597 (1991).

In the present application, the term "single-strand antibody" (scFv) refers usually to a molecule formed by linking an antibody heavy chain variable region to a light chain variable region via an oligopeptide linker.

In the present application, the term "chimeric antibody" refers usually to an antibody in which a portion of each heavy chain or light chain amino acid sequence is homologous to the corresponding amino acid sequence in the antibody from a specific species, or belongs to a specific category, and the rest of the chain is homologous to the corresponding sequence in another species. For example, the variable region of the light chain and the heavy chain are both derived from the variable region of an animal species (such as, mouse, rat, etc.), while the constant portion is homologous to an antibody sequence from another species (such as, human). For example, to obtain chimeric antibodies, the variable regions may be produced by use of non-human-derived B cells or hybridoma cells, and the constant region combined therewith is derived from human. The variable region has an advantage of easy production, and its specificity is not affected by the source of the constant region combined therewith. At the same time, since the constant region of the chimeric antibody may be derived from human, the possibility of the antibody evoking an immune response upon injection is lower than that of an antibody in which the constant region is derived from a non-human source.

In the present application, the term "humanized antibody" refers usually to a chimeric antibody, which contains fewer sequences derived from non-human immunoglobulin proteins, so as to reduce the immunogenicity when a heterologous antibody is introduced into humans, and maintain the complete antigen binding affinity and specificity of the antibody. For example, CDR grafting (Jones et al., Nature 321:522 (1986)) and its variants may be used; comprising "reshaping" (Verhoeyen, et al., 1988 Science 239:1534-1536; Riechmann, et al., 1988 Nature 332:323-337; Tempest, et al., Bio/Technol 1991 9:266-271), "hyperchimerization", (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154) and "Veneering", (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312), surface reconstruction (U.S. Pat. No. 5,639,641) and other technical means to humanize the binding domains from non-human sources. If other regions, such as, hinge regions and constant region domains are also derived from non-human sources, these areas may also be humanized.

In the present application, the term "epitope" refers usually to an antigenic determinant, that is, the moiety of a molecule that is recognized by the immune system (for example, by an antibody). For example, the epitope may be discontinuous three-dimensional sites in an antigen recognized by the immune system. Epitopes consist usually of chemically active surface groups of molecules (such as, amino acids or sugar side chains), and usually have specific three-dimensional structural characteristics as well as specific charge characteristics. Epitopes may be divided into conformational epitopes and non-conformational epitopes (linear epitopes) according to their structures. The epitopes may be composed of continuous residues, or may be formed by discrete residues which become adjacent due to the folding of the antigen polymer.

In the present application, the term "IgG" refers usually to immunoglobulin G. IgG is one of the human immunoglobulins, which further comprise IgA, IgM, IgD and IgE. According to the antigenic difference of the y chain in the IgG molecule, the human IgG has four subtypes: IgG1, IgG2, IgG3, IgG4. IgG plays an important role in immune. In the present application, the term "IgG1" refers usually to the subtype with the highest proportion of IgG which has high affinity with an Fc receptor.

In the present application, the term "nucleic acid molecule" refers usually to an isolated nucleotide, deoxyribonucleotide, ribonucleotide or an analog thereof with any length that may be isolated from its natural environment or artificially synthesized.

In the present application, the term "vector" refers usually to a nucleic acid molecule capable of self-replication in a suitable host. The vector may transfer the inserted nucleic acid molecule to cells and/or between cells. The vector may comprise those primarily used for inserting DNA or RNA into the cell, primarily used for copying the DNA or RNA, and primarily used for the transcription of DNA or RNA and/or the expression of translation. The vector may be a polynucleotide that may be transcribed and translated to a peptide when being introduced into a suitable cell. Usually, the vector may produce a desired expression product by culturing appropriate cells which comprise the vector.

In the present application, the term "cell" refers usually to an individual cell, cell line or cell culture that may comprise or may have comprised a plasmid or a vector comprising the nucleic acid molecule of the present application, or may express the antibody or an antigen-binding fragment thereof in the present application. The cell may comprise the progeny of a single cell. Due to natural, accidental or deliberate mutation, the progeny cell may not be completely identical to the original parent cell in morphology or in the genome, as long as the progeny cell may express the antibody or an antigen-binding fragment thereof in the present application. The cell may be obtained by transfecting cells in vitro with the vector of the present application. The cell may be a prokaryotic cell (such as, *E. coli*), or it may also be a eukaryotic cell (such as, yeast cell, e.g., COS cell, Chinese hamster ovary (CHO) cell, HeLa cell, HEK293 cell, COS-1 cell, NS0 cell or myeloma cell). In some embodiments, the cell is a mammalian cell. For example, the mammalian cell may be a CHO-K1 cell. In the present application, the term "recombinant cell" refers usually to a cell into which a recombinant expression vector has been introduced. The recombinant cell not only comprises a certain specific cell, but also comprises the progeny of these cells.

In the present application, the terms "protein A" and "ProA" are interchangeably used herein, and comprise protein A recovered from their natural source, protein A produced by synthesis (e.g., by peptide synthesis or by recombinant technology), and variants that retain the binding ability of the protein. The protein A may be purchased from Repligen, Pharmacia and Fermatech. The protein A is usually immobilized on a solid-phase support material. The term "ProA" also refers to a column of affinity chromatography resin or a chromatographic solid support matrix with protein A covalently linked thereto.

In the present application, the term "about" refers usually to a variation within 0.5%-10% of a specified value, such as, a variation within 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the specified number.

In the present application, the term "comprise/comprising" usually means comprising, including, containing or encompassing. In some cases, the term also means "is/are" or "be composed of".

Antibody, Antibody-Binding Fragment Thereof, or Variant

In an aspect, the present application provides an antibody or an antigen-binding fragment thereof or a variant thereof, which binds to the CD38 protein at a $K_D$ value of $1 \times 10^{-9}$M or below (e.g., a $K_D$ value of not greater than about $1 \times 10^{-9}$M, not greater than about $9 \times 10^{-10}$M, not greater than about $8 \times 10^{-10}$M, not greater than about $7 \times 10^{-10}$M, not greater than about $6 \times 10^{-10}$M, not greater than about $5 \times 10^{-10}$M, not greater than about $4 \times 10^{-10}$M, not greater than about $3 \times 10^{-10}$M, not greater than about $2 \times 10^{-10}$M, not greater than $1 \times 10^{-10}$M or not greater than about $1 \times 10^{-11}$M or below).

The antibody or the antigen-binding fragment thereof in the present application may kill CD38+ cells by means of antibody-dependent cell-mediated cytotoxicity (ADCC), complement-dependent cytotoxicity (CDC) and/or apoptosis.

The antibody or the antigen-binding fragment thereof or the variant in the present application may kill and damage tumor cells and/or inhibit tumor growth by specifically binding to the CD38 protein. For example, the tumor may comprise a CD38 positive tumor. For example, the CD38 positive tumor may be selected from the group comprising multiple myeloma, lymphoma and leukemia. Alternatively, for example, the tumor is selected from the group comprising non-Hodgkin lymphoma and Hodgkin's lymphoma. The tumor cell may be selected from the group comprising Raji cell, Daudi cell, Ramos cell and RPMI8226 cell. In the present application, the antibody or an antigen-binding fragment thereof may kill and damage multiple myeloma, lymphoma, leukemia, non-Hodgkin lymphoma and Hodgkin's lymphoma cells or inhibit the growth of multiple myeloma, lymphoma, leukemia, non-Hodgkin lymphoma and Hodgkin's lymphoma.

The antibody or an antigen-binding fragment thereof in the present application may bind to one or more residues corresponding to amino acid residues 60-89 of the human CD38 protein when binding to the C38 protein. For example, the amino acid residues 60-89 of the human CD38 protein are as shown in SEQ ID NO:15.

In the present application, the antibody or an antigen-binding fragment thereof may also bind to the amino acid residues corresponding to amino acid residues 90-119 of the human CD38 protein, corresponding to amino acid residues 150-159 of the human CD38 protein, or corresponding to amino acid residues 180-189 of the human CD38 protein.

In the present application, the antibody or the antigen-binding fragment thereof may not substantially bind to the amino acid residues corresponding to amino acid residues 170-179 of the human CD38 protein, or not bind to the amino acid residues corresponding to amino acid residues 291-300 of the human CD38 protein.

The antibody of the present application may be monoclonal antibody, single-strand antibody, chimeric antibody, humanized antibody and/or fully human antibody. The antigen-binding fragment of the antibody of the present application may be Fab, Fab', F(ab)2, F(ab')2, Fv and/or ScFv fragment.

The CD38 protein of the present application may be human CD38 protein or monkey CD38 protein. For example, the CD38 protein may not be mouse CD38 protein, or may not be rat CD38 protein. In some embodiments, the antibody or an antigen-binding fragment thereof in the present application does not substantially bind to mouse CD38 protein or rat CD38 protein.

The antibody or the antigen-binding fragment thereof in the present application may compete with a reference antibody to bind to the CD38 protein. The reference antibody may comprise a light chain variable region and a heavy chain variable region. For example, the light chain variable region of the reference antibody may comprise LCDR1, LCDR2 and LCDR3, the LCDR1 may comprise an amino acid sequence as shown in SEQ ID NO:1; the LCDR2 may comprise an amino acid sequence as shown in SEQ ID NO:2; the LCDR3 may comprise an amino acid sequence as shown in SEQ ID NO:3, the heavy chain variable region of the reference antibody may comprise HCDR1, HCDR2 and HCDR3, the HCDR1 may comprise an amino acid sequence as shown in SEQ ID NO:4; the HCDR2 may comprise an amino acid sequence as shown in SEQ ID NO:5; and the HCDR3 may comprise an amino acid sequence as shown in SEQ ID NO:6.

In the present application, the amino acid sequence of the light chain variable region of the reference antibody may comprise an amino acid sequence as shown in SEQ ID NO:7, and the amino acid sequence of the heavy chain variable region of the reference antibody may comprise an amino acid sequence as shown in SEQ ID NO:8.

In the present application, the light chain of the reference antibody may comprise an amino acid sequence as shown in SEQ ID NO:22; for example, the light chain of the reference antibody may comprise an amino acid sequence as shown in any one of SEQ ID NO:11, SEQ ID NO:16, SEQ ID NO:18 and SEQ ID NO:20. The heavy chain of the reference antibody may comprise an amino acid sequence as shown in SEQ ID NO:23; for example, the heavy chain of the reference antibody may comprise an amino acid sequence as shown in any one of SEQ ID NO:13, SEQ ID NO:17, SEQ ID NO:19 and SEQ ID NO:21.

For instance, the light chain of the reference antibody may comprise an amino acid sequence as shown in SEQ ID NO:11, and the heavy chain of the reference antibody may comprise an amino acid sequence as shown in SEQ ID NO:13. For example, the light chain of the reference antibody may comprise an amino acid sequence as shown in SEQ ID NO:16, and the heavy chain of the reference antibody may comprise an amino acid sequence as shown in SEQ ID NO:17. For example, the light chain of the reference antibody may comprise an amino acid sequence as shown in SEQ ID NO:18, and the heavy chain of the reference antibody may comprise an amino acid sequence as shown in SEQ ID NO:19. For example, the light chain of the reference antibody may comprise an amino acid sequence as shown in SEQ ID NO:20, and the heavy chain of the reference antibody may comprise an amino acid sequence as shown in SEQ ID NO:21.

The antibody or the antigen-binding fragment thereof according to the present application may comprise the light chain of the antibody or the fragment thereof.

For instance, the light chain of the antibody or the fragment thereof may comprise LCDR1, and the LCDR1 may comprise an amino acid sequence as shown in SEQ ID NO:1. The light chain of the antibody or the fragment thereof may comprise LCDR2, and the LCDR2 may comprise an amino acid sequence as shown in SEQ ID NO:2. The light chain of the antibody or the fragment thereof may comprise LCDR3, and the LCDR3 may comprise an amino acid sequence as shown in SEQ ID NO:3.

The light chain of the antibody or the fragment thereof of the present application may comprise a light chain variable region VL, and the light chain variable region VL may comprise an amino acid sequence as shown in SEQ ID NO:7.

In the present application, the light chain of the antibody or the fragment thereof may comprise an Igκ constant region, e.g., it may comprise a human Igκ constant region.

In the present application, the light chain of the antibody or the fragment thereof may comprise an amino acid sequence as shown in SEQ ID NO:22: EIVMTQSPASLSASLGQRAX$^{20}$ISCRASX$^{27}$SVSX$^{31}$SAX$^{34}$SYVHWYQQKSGQPPKLLIYLASX$^{57}$X$^{58}$X$^{59}$SG-VPARFSGSGSGTDFTLTIIPVESEDVATYYCHHSRX$^{97}$X$^{98}$PX$^{100}$X$^{101}$FGSGTK LEIKRTVAAPSVFIFPPSD-EQLKSGTASVVCLLNNFYPREAKVQWKVD-NALQSGNSQES VTEQDSKDSTYSLSSTLTL-SKADYEKHKVYACEVTHQGLSSPVTKSFNRGEC (SEQ ID NO:22), wherein $X^{20}$=T or S; $X^{27}$=S or N; $X^{31}$=S or T; $X^{34}$=F or Y; $X^{57}$=N and D; $X^{58}$=L or I; $X^{59}$=E or Q; $X^{97}$=E or Q; $X^{98}$=L or V; $X^{100}$=F or S; $X^{101}$=T or S.

In some embodiments, as compared with the light chain of the antibody shown in SEQ ID NO:11, the light chain of the antibody or the fragment thereof at least comprises an amino acid substitution selected from the group comprising:

(a) amino acid substitution(s) at $X^{20}$, $X^{27}$, $X^{34}$, $X^{58}$, $X^{59}$, $X^{97}$ and/or $X^{100}$;

(b) amino acid substitution(s) at $X^{34}$, $X^{5}$, $X^{59}$, $X^{100}$ and/or $X^{101}$; and (c) amino acid substitution(s) at $X^{27}$, $X^{31}$ and/or $X^{98}$.

In some embodiments, as compared with the light chain of the antibody shown in SEQ ID NO:11, the light chain of the antibody or the fragment thereof at least comprises amino acid substitution(s) at $X^{20}$, $X^{27}$, $X^{34}$, $X^{58}$, $X^{59}$, $X^{97}$ and/or $X^{100}$, wherein, the amino acid at $X^{20}$ may be substituted with T or S; the amino acid at $X^{27}$ may be substituted with S or N; the amino acid at $X^{34}$ may be substituted with F or Y; the amino acid at $X^{58}$ may be substituted with L or I; the amino acid at $X^{59}$ may be substituted with E or Q; the amino acid at $X^{97}$ may be substituted with E or Q; and the amino acid at $X^{100}$ may be substituted with F or S.

In some embodiments, as compared with the light chain of the antibody shown in SEQ ID NO:11, the light chain of the antibody or the fragment thereof at least comprises amino acid substitution(s) at $X^{34}$, $X^{57}$, $X^{59}$, $X^{100}$ and/or $X^{101}$, wherein, the amino acid at $X^{34}$ may be substituted with F or Y; the amino acid at $X^{57}$ may be substituted with N or D; the amino acid at $X^{59}$ may be substituted with E or Q; the amino acid at $X^{100}$ may be substituted with F or S; and the amino acid at $X^{101}$ may be substituted with T or S.

In some embodiments, as compared with the light chain of the antibody shown in SEQ ID NO:11, the light chain of the antibody or the fragment thereof at least comprises amino acid substitution(s) at $X^{27}$, $X^{31}$ and/or $X^{98}$, wherein, the amino acid at $X^{27}$ may be substituted with S or N; the amino acid at $X^{31}$ may be substituted with S or T; and the amino acid at $X^{98}$ may be substituted with L or V.

For instance, the light chain of the antibody or the fragment thereof may comprise an amino acid sequence as shown in any one of SEQ ID NO:11, SEQ ID NO:16, SEQ ID NO:18 and SEQ ID NO:20.

The antibody or the antigen-binding fragment thereof in the present application may comprise a heavy chain of the antibody or a fragment thereof.

In the present application, the heavy chain of the antibody or the fragment thereof may comprise HCDR1, and the HCDR1 may comprise an amino acid sequence as shown in SEQ ID NO:4. The heavy chain of the antibody or the fragment thereof may comprise HCDR2, and the HCDR2 may comprise an amino acid sequence as shown in SEQ ID NO:5. Alternatively, for example, the heavy chain of the antibody or the fragment thereof may comprise HCDR3, and the HCDR3 may comprise an amino acid sequence as shown in SEQ ID NO:6.

The heavy chain of the antibody or the fragment thereof may comprise a heavy chain variable region VH, and the heavy chain variable region VH may comprise an amino acid sequence as shown in SEQ ID NO:8.

In the present application, the heavy chain of the antibody or the fragment thereof further comprises a human constant region. For example, the human constant region may comprise a human IgG constant region. For example, the IgG constant region may comprise a human IgG1 constant region.

In the present application, the heavy chain of the antibody or the fragment thereof may comprise an amino acid sequence as shown in SEQ ID NO:23: QVQLLESGGGLVQPGGSLKLSCVASGX$^{27}$X$^{28}$FSLYX$^{33}$MNWVRQAPGKGLEWIGKIX$^{52}$PX$^{54}$SSX$^{57}$X$^{58}$X$^{59}$YX$^{61}$PSX$^{64}$KDKFFISRDNAKNTLYLQMTKVRSEDTALYYCARLX$^{100}$IX$^{102}$X$^{103}$GGX$^{106}$X$^{107}$YWGQGTTLTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLSLSPGK (SEQ ID NO:23), wherein $X^{27}$=F or Y; $X^{28}$=D or N; $X^{33}$=W or Y; $X^{52}$=N, Q or S; $X^{54}$=D, E or N; $X^{57}$=T or S; $X^{58}$=I or L; $X^{59}$=N or Q; $X^{61}$=T or S; $X^{64}$=L or V; $X^{100}$=W or Y; $X^{102}$=A or G; $X^{103}$=T or S; $X^{106}$=F or Y; $X^{107}$=D or N.

In some embodiments, as compared with the light chain of the antibody shown in SEQ ID NO: 13, the light chain of the antibody or the fragment thereof at least comprises amino acid substitution(s) selected from the group comprising:

(a) amino acid substitution(s) at $X^{27}$, $X^{28}$, $X^{33}$, $X^{52}$, $X^{54}$, $X^{59}$, $X^{102}$ and/or $X^{103}$;

(b) amino acid substitution(s) at X, $X^{54}$, $X^{61}$, $X^{100}$ and/or X1$^{03}$; and (c) amino acid substitution(s) at X, $X^{57}$, $X^{58}$, $X^{64}$, $X^{106}$ and/or $X^{107}$.

In some embodiments, as compared with the light chain of the antibody shown in SEQ ID NO: 13, the light chain of the antibody or the fragment thereof at least comprises amino acid substitution(s) at $X^{27}$, $X^{28}$, $X^{33}$, $X^{52}$, $X^{54}$, $X^{59}$, $X^{102}$ and/or $X^{103}$, wherein, the amino acid at $X^{27}$ may be substituted with F or Y; the amino acid at $X^{28}$ may be substituted with D or N; the amino acid at $X^{33}$ may be substituted with W or Y; the amino acid at $X^{52}$ may be substituted with N or Q; the amino acid at $X^{54}$ may be substituted with D or E; the amino acid at $X^{59}$ may be substituted with N or Q; the amino acid at $X^{102}$ may be substituted with A or G; and the amino acid at $X^{103}$ may be substituted with T or S.

In some embodiments, as compared with the light chain of the antibody shown in SEQ ID NO: 13, the light chain of the antibody or the fragment thereof at least comprises amino acid substitution(s) at $X^{52}$, $X^{54}$, $X^{61}$, $X^{100}$ and/or $X^{103}$, wherein, the amino acid at $X^{52}$ may be substituted with N or S; the amino acid at $X^{54}$ may be substituted with D or N; the amino acid at $X^{61}$ may be substituted with T or S; the amino acid at $X^{100}$ may be substituted with W or Y; and the amino acid at $X^{103}$ may be substituted with T or S.

In some embodiments, as compared with the light chain of the antibody shown in SEQ ID NO: 13, the light chain of the antibody or the fragment thereof at least comprises amino acid substitution(s) at $X^{52}$, $X^{57}$, $X^{58}$, $X^{64}$, $X^{106}$ and/or $X^{107}$, wherein, the amino acid at $X^{52}$ may be substituted with N or S; the amino acid at $X^{57}$ may be substituted with T or S; the amino acid at $X^{58}$ may be substituted with I or L; the amino acid at $X^{64}$ may be substituted with L or V; the amino acid at $X^{106}$ may be substituted with F or Y; and the amino acid at $X^{107}$ may be substituted with D or N.

In some embodiments, the heavy chain of the antibody may comprise an amino acid sequence as shown in any one of SEQ ID NO:13, SEQ ID NO:17, SEQ ID NO:19 and SEQ ID NO:21.

In some embodiments, in the antibody or the antigen-binding fragment thereof in the present application, LCDR1 may comprise an amino acid sequence as shown in SEQ ID NO:1 or a variant thereof, the LCDR2 may comprise an amino acid sequence as shown in SEQ ID NO:2 or a variant thereof, the LCDR3 may comprise an amino acid sequence as shown in SEQ ID NO:3 or a variant thereof, and HCDR1 may comprise an amino acid sequence as shown in SEQ ID NO:4 or a variant thereof, HCDR2 may comprise an amino acid sequence as shown in SEQ ID NO:5 or a variant thereof, HCDR3 may comprise an amino acid sequence as shown in SEQ ID NO:6 or a variant thereof. For example, the antibody or an antigen-binding fragment thereof may comprise the antibody SG003 or an antibody having the same LCDR1-3 and HCDR1-3 therewith. In some embodiments, the light chain of the antibody or an antigen-binding fragment thereof in the present application may comprise a light chain variable region, the light chain variable region may comprise an amino acid sequence as shown in SEQ ID NO:7 or a variant thereof, and the heavy chain may comprise a heavy chain variable region, the heavy chain variable region may comprise an amino acid sequence as shown in SEQ ID NO:8 or a variant thereof. For example, the antibody or an antigen-binding fragment thereof may comprise the antibody SG003 or an antibody having the same light chain variable region and heavy chain variable region therewith. In some embodiments, the antibody or an antigen-binding fragment thereof in the present application may comprise a light chain and a heavy chain, the light chain may comprise an amino acid sequence as shown in SEQ ID NO:11, and the heavy chain may comprise an amino acid sequence as shown in SEQ ID NO:13. For example, the antibody or the antigen-binding fragment thereof may comprise the antibody SG003 or an amino acid sequence having the same light chain and heavy chain therewith.

In some embodiments, the antibody of the present application may be SG003. The LCDR1, LCDR2 and LCDR3 of the antibody SG003 may comprise amino acid sequences as shown in SEQ ID NO.1, SEQ ID NO.2 and SEQ ID NO.3, respectively; VL may comprise the amino acid sequence as shown in SEQ ID NO.7; HCDR1, LCDR2 and LCDR3 may comprise the amino acid sequences as shown in SEQ ID NO.4, SEQ ID NO.5 and SEQ ID NO.6, respectively; VH may comprise the amino acid sequence as shown in SEQ ID NO.8; the light chain may comprise the amino acid sequence as shown in SEQ ID NO.11; and the heavy chain may comprise the amino acid sequence as shown in SEQ ID NO.13.

In some embodiments, the antibody or an antigen-binding fragment thereof in the present application compete with a reference antibody to bind to CD38 protein (e.g., human CD38 protein or monkey CD38 protein). The reference antibody may comprise LCDR1, LCDR2, LCDR3 and HCDR1, HCDR2, HCDR3, and the LCDR1 may comprise the amino acid sequence as shown in SEQ ID NO:1; the LCDR2 may comprise the amino acid sequence as shown in SEQ ID NO:2; the LCDR3 may comprise the amino acid sequence as shown in SEQ ID NO:3; the HCDR1 may comprise the amino acid sequence as shown in SEQ ID NO:4; the HCDR2 may comprise the amino acid sequence as shown in SEQ ID NO:5; and the HCDR3 may comprise the amino acid sequence as shown in SEQ ID NO:6. In some embodiments, the reference antibody may comprise the antibody SG003 or an antibody having the same LCDR1, LCDR2, LCDR3 and HCDR1, HCDR2, HCDR3 therewith. In some embodiments, the reference antibody may comprise a light chain variable region and a heavy chain variable region, the light chain variable region may comprise the amino acid sequence as shown in SEQ ID NO:7; and the heavy chain variable region may comprise the amino acid sequence as shown in SEQ ID NO:8. For example, the antibody or an antigen-binding fragment thereof may comprise the antibody SG003 or an antibody having the same light chain variable region and heavy chain variable region therewith. In some embodiments, the reference antibody may comprise a light chain and a heavy chain, the light chain may comprise an amino acid sequence as shown in SEQ ID NO:11 and the heavy chain may comprise the amino acid sequence as shown in SEQ ID NO:13. For instance, the reference antibody or the antigen-binding fragment thereof may comprise the antibody SG003 or an antibody having the same light chain and heavy chain therewith.

The antibody or the antigen-binding fragment thereof in the present application may further comprise, in the amino acid sequences of the light chain and/or the heavy chain thereof, one or more random mutation (e.g., one or more, one or several amino acid substitutions). For instance, the antibody or an antigen-binding fragment thereof may comprise, at one or more sites in the frame region L-FR1~L-FR4 of its light chain variable region, one or more random mutation (e.g., one or more, one or several amino acid substitutions), and/or comprise, at one or more sites in the frame region H-FR1~H-FR4 of its heavy chain variable region, one or more random mutation (e.g., one or more, one or several amino acid substitutions). For instance, upon random mutation, the light chain of the antibody or the antigen-binding fragment thereof may comprise an amino acid sequence as shown in any one of SEQ ID NO:16, SEQ ID NO:18 and SEQ ID NO:20; and/or, the heavy chain of the antibody or an antigen-binding fragment thereof may comprise an amino acid sequence as shown in any one of SEQ ID NO:17, SEQ ID NO:19 and SEQ ID NO:21. The randomly mutated CD38 antibody or an antigen-binding fragment thereof still has an ability of specifically binding to human CD38 protein and monkey CD38 protein.

In some embodiments, the light chain of the antibody or an antigen-binding fragment thereof in the present application may comprise the amino acid sequence as shown in SEQ ID NO:16; and the heavy chain may comprise the amino acid sequence as shown in SEQ ID NO:17; alternatively, the light chain of the antibody or an antigen-binding fragment thereof in the present application may comprise the amino acid sequence as shown in SEQ ID NO:18; and the heavy chain may comprise the amino acid sequence as shown in SEQ ID NO:19; alternatively, the light chain of the antibody or the antigen-binding fragment thereof in the present application may comprise the amino acid sequence as shown in SEQ ID NO:20; and the heavy chain may comprise the amino acid sequence as shown in SEQ ID NO:21.

The proteins, peptides and/or amino acid sequences involved in the present application should also be understood as encompassing the following scope: a variant or a homologue having the same or similar function with the protein or peptide.

In the present application, the variant may be a protein or peptide obtained by substitution, deletion, or addition of one or more amino acids with respect to the amino acid sequences of the protein and/or peptide (e.g., the antibody or the fragment thereof that specifically binds to the CD38 protein). For example, the functional variant may comprise a protein or peptide with amino acid modification by substitution, deletion and/or insertion of at least one, e.g., 1-30, 1-20, or 1-10, or e.g., 1, 2, 3, 4 or 5 amino acids. The functional variant may basically remain the biological activity of the protein or peptide prior to modification (e.g., substitution, deletion or addition). For example, the functional variant may remain at least 60%, 70%, 80%, 90%, or 100% of the biological activity (such as, antigen-binding ability) of the original protein or peptide. For example, the substitution may be a conservative substitution.

In the present application, the homologue may be a protein or peptide having at least about 85% (e.g., at least about 85%, about 90%, about 91%, about 92%, about 93%, about 94%, about 95%, about 96%, about 97%, about 98%, about 99% or greater) sequence homology with the amino acid sequence of the protein and/or peptide (e.g., the antibody or the fragment thereof that specifically binds to the CD38 protein).

In the present application, the homology refers usually to the similarity, analogy, or association between two or more sequences. The "sequence homology percentage" may be calculated as follows: the two sequences to be aligned are compared in the comparison window, to determine the number of positions with the same nucleic acid base (e.g., A, T, C, G, I) or the same amino acid residue (e.g., Ala, Pro, Ser, Thr, Gly, Val, Leu, Ile, Phe, Tyr, Trp, Lys, Arg, His, Asp, Glu, Asn, Gln, Cys and Met) in two sequences to obtain the number of matching positions. The number of the matching positions is divided by the total number of positions in the comparison window (that is, the window size), and the result is multiplied by 100 to produce the sequence homology percentage. The alignment for determining the sequence homology percentage may be carried out in accordance with various methods that are known in the art, such as, using publicly available computer software, such as, BLAST, BLAST-2, ALIGN or Megalign (DNASTAR) softwares. Those skilled in the art may determine appropriate parameters for aligning sequences, comprising any algorithm required to achieve maximum alignment within the full-length sequence scope being compared or within the target sequence area. The homology may also be determined by the following method: FASTA and BLAST. For the description of the FASTA algorithm, may refer to W. R. Pearson and D. J. Lipman's "Improved Tools for Biological Sequence Comparison", Proceedings of the National Academy of Sciences (Proc. Natl. Acad. Sci.), 85: 2444-2448, 1988; and D. J. Lipman and W. R. Pearson's "Fast and Sensitive Protein Mass Similarity Search", Science, 227: 1435-1441, 1989. For the description of the BLAST algorithm, may refer to S. Altschul, W. Gish, W. Miller, E. W. Myers and D. Lipman, "A Basic Local Alignment Search Tool", Journal of Molecular Biology, 215: 403-410, 1990.

Nucleic Acid, Vector, Cell, and Preparation Method

In another aspect, the present application further provides one or more isolated nucleic acid molecules. The one or more nucleic acid molecules may comprise a polynucleotide encoding the antibody or an antigen-binding fragment thereof according to the present application. For example, the polynucleotide in one or more nucleic acid molecules may encode the whole antibody or an antigen-binding fragment thereof, and may also encode a portion thereof (e.g., one or more of HCDR1-3, LCDR1-3, VL, VH, the light chain or the heavy chain).

The at least one of the nucleic acid molecules of the nucleic acid molecule of the present application may be codon optimized. For example, the codon optimization method comprises, but is not limited to: eliminating rare codons, adjusting the GC content, increasing the stability of mRNA, adjusting the secondary structure of mRNA, rationally designing the linker and adjusting the start codon environment.

In some embodiments, the nucleic acid molecule may comprise one or more polynucleotide sequences selected from the group comprising SEQ ID NO:9, SEQ ID NO:10, SEQ ID NO:12 and SEQ ID NO:14. wherein SEQ ID NO:9 may encode the light chain variable region of the antibody SG003 of the present application. SEQ ID NO:10 may encode the heavy chain variable region of the antibody SG003 of the present application. SEQ ID NO:12 may encode the light chain of the antibody SG003 of the present application. SEQ ID NO:14 may encode the heavy chain of the antibody SG003 of the present application.

The nucleic acid molecule of the present application may be isolated. For example, the nucleic acid molecule may be produced or synthesized by the following methods: (i) the nucleic acid molecule may be in vitro amplificated, such as, produced by polymerase chain reaction (PCR) amplification, (ii) the nucleic acid molecule may be produced by cloning and recombination, (iii) the nucleic acid molecule may be purified, such as, separated by digestion and gel electrophoretic fractionation, or (iv) the nucleic acid molecule may be synthesized, such as, by chemical synthesis. In some embodiments, the isolated nucleic acid is a nucleic acid molecule prepared by a recombinant DNA technology.

In the present application, the nucleic acid encoding the antibody or an antigen-binding fragment thereof may be prepared through various methods known in the art. These methods comprise, but not limited to, restrictive fragment operation or overlap extension PCR using synthetic oligonucleotides, may refer to the following for details: Sambrook et al., Molecular Cloning, A Laboratory Manual, Cold Spring Harbor Laboratory Press, Cold Spring Harbor, N.Y., 1989; and Ausube et al., Current Protocols in Molecular Biology, Greene Publishing and Wiley-Interscience, New York N.Y., 1993.

In another aspect, the present application provides one or more vectors which comprise one or more nucleic acid molecules of the present application. Each vector may comprise one or more nucleic acid molecules. Moreover, the vector may further comprise other genes, such as, a label gene that allows to select the vector in appropriate cells and under appropriate conditions. Moreover, the vector may further comprise an expression control element that allows the encoding region to be appropriately expressed in an appropriate host. Such control element is well known by persons skilled in the art, such as, the control element may comprise promoter, ribosome binding site, enhancer and other control elements adjusting gene transcription or mRNA translation, etc. In some embodiments, the expression control sequence is an adjustable element. The specific structure of the expression control sequence may vary depending on the functions of species or cell types, but usually comprises 5' non-transcribed sequence and 5' and 3' non-translated sequences involved in transcription and translation initiation, such as, TATA box, capping sequence, CAAT sequence, etc. For example, the 5' non-transcribed expression control sequence may comprise a promoter region, and the promoter region may comprise a promoter sequence for transcriptionally controlling a functional linking nucleic acid. The expression control sequence may also comprise an enhancer sequence or an upstream activator sequence. One or more nucleic acid molecules of the present application may be operably linked to the expression control element.

The vector may comprise, e.g., plasmids, cosmids, viruses, bacteriophages or other vectors commonly used in for example genetic engineering. For example, the vector is an expression vector. For example, the expression vector may be T-easy.

In another aspect, the present application provides a cell which may comprise one or more of the nucleic acid molecules of the present application and/or one or more vectors of the present application. In some embodiments, each or each kind of cell may comprise one or one kind of nucleic acid molecule or vector of the present application. In some embodiments, each or each kind of cell may comprise more than one (e.g., two or more) or more than one kind of (e.g., two or more kinds of) nucleic acid molecules or vectors of the present application. For example, the vector of the present application may be introduced into a cell, such as, eukaryotic cells, such as plant-derived cells, fungal or yeast cells, etc. The vector of the present application may be introduced into the cell by a method known in the art, such as, electroporation, lipofectine transfection, lipofectamin transfection, etc. For example, the cell may be CHO-S.

In another aspect, the present application provides a method for preparing an antibody or an antigen-binding fragment thereof. The method may comprise culturing the cell of the present application under conditions which allow to express the antibody or an antigen-binding fragment thereof. For example, it is feasible to use appropriate culture media, appropriate temperature and incubation time, and so on. These methods are known by persons of ordinary skills in the art.

In some cases, the method may further comprise a step of isolating and/or purifying the antibody or antigen-binding fragment thereof. For example, protein G-agarose or protein A-agarose may be used for affinity chromatography, and gel antibodies and/or high-performance liquid chromatography and the like may also be used to purify and isolate the antibodies or antigen-binding fragments of the present application. For example, protein A affinity purification may also be used.

Pharmaceutical Composition, Application

In another aspect, the present application provides a pharmaceutical composition which may comprise the antibody, an antibody-binding fragment or a variant thereof of the present application, a nucleic acid molecule, a vector, or a cell, and an optionally pharmaceutically acceptable adjuvant.

The pharmaceutically acceptable adjuvant may comprise buffers, antioxidants, preservatives, low molecular weight peptides, proteins, hydrophilic polymers, amino acids, sugars, chelating agents, counterions, metal complexes and/or non-ionic surfactants, etc.

In the present application, the pharmaceutical composition may be formulated for oral administration, intravenous administration, intramuscular administration, in situ administration at the tumor site, inhalation, rectal administration, vaginal administration, transdermal administration or administration via subcutaneous depot.

The pharmaceutical composition may be used to inhibit tumor growth. For example, the pharmaceutical composition of the present application may inhibit or alleviate the development or progression of diseases, reduce the tumor size (or even basically eliminate the tumor), and/or reduce and/or stabilize the disease state.

The pharmaceutical composition of the present application may comprise a therapeutically effective amount of the antibody or the antigen-binding fragment thereof. The therapeutically effective amount may be a dose required to prevent and/or treat (at least partially treat) a disorder or condition (e.g. cancer) and/or any complications in a subject with or at risk of development of the disorder or condition.

On the other hand, the present application provides an application of the antibody or an antigen-binding fragment thereof in preparation of medicaments for preventing or treating tumors.

On the other hand, the present application provides an antibody or an antigen-binding fragment thereof for preventing or treating tumors.

On the other hand, the present application provides a method for preventing or treating tumors. The method comprises administering to a subject in need the antibody or an antigen-binding fragment thereof, the molecular nucleic acid, the vector, the cell and/or the pharmaceutical composition in the present application.

In the present application, the tumors may comprise a CD38 positive tumor. For example, the CD38 positive tumor may be selected from the group comprising multiple myeloma, lymphoma and leukemia.

In some embodiments, the tumor is selected from the group comprising non-Hodgkin lymphoma and Hodgkin's lymphoma.

On the other hand, the present application provides a method for inhibiting the binding of CD38 protein to CD38 ligand, and the method comprises administering the antibody or an antigen-binding fragment thereof, the nucleic acid molecule, the vector and/or the cell in the present application.

In the present application, the CD38 ligand may comprise a CD31 protein.

In some embodiments, the method for inhibiting the binding of CD38 protein to CD38 ligand is an in vitro or ex vivo method.

The present application may comprise the following embodiment:

1. An antibody or an antigen-binding fragment thereof, which binds to a CD38 protein at a $K_D$ value of $1 \times 10^{-9}$M or below.

2. The antibody or an antigen-binding fragment thereof according to embodiment 1, which can kill and damage tumor cells and/or inhibit tumor growth by specifically binding to the CD38 protein.

3. The antibody or the antigen-binding fragment thereof according to any one of embodiments 1-2, which can kill $CD38^+$ cells by antibody-dependent cell-mediated cytotoxicity (ADCC), complement-dependent cytotoxicity (CDC) and/or apoptosis.

4. The antibody or the antigen-binding fragment thereof according to embodiment 3, wherein the tumors comprise a CD38 positive tumor.

5. The antibody or the antigen-binding fragment thereof according to embodiment 4, wherein the CD38 positive tumor is selected from the group comprising multiple myeloma, lymphoma and leukemia.

6. The antibody or the antigen-binding fragment thereof according to any one of embodiments 3-5, wherein the tumor is selected from the group comprising non-Hodgkin lymphoma and Hodgkin's lymphoma.

7. The antibody or the antigen-binding fragment thereof according to any one of embodiments 3-6, wherein the tumor cells comprise those selected from the group comprising Raji cell, Daudi cell, Ramos cell and RPMI8226 cell.

8. The antibody or the antigen-binding fragment thereof according to any one of embodiments 1-7, which binds to one or more residues corresponding to amino acid residues 60-89 of the human CD38 protein when binding to the CD38 protein.

9. The antibody or the antigen-binding fragment thereof according to any one of embodiments 1-8, wherein the antibody is selected from the group comprising monoclonal antibody, single-strand antibody, chimeric antibody, humanized antibody and fully human antibody.

10. The antibody or the antigen-binding fragment thereof according to any one of embodiments 1-9, wherein the antigen-binding fragment is selected from the group comprising Fab, Fab', F(ab)2, F(ab')2, Fv and ScFv fragments.

11. The antibody or the antigen-binding fragment thereof according to any one of embodiments 1-10, wherein the CD38 protein is human CD38 protein or monkey CD38 protein.

12. The antibody or the antigen-binding fragment thereof according to any one of embodiments 1-11, which competes with a reference antibody to bind to the CD38 protein, wherein the reference antibody comprises a light chain variable region and a heavy chain variable region, the light chain variable region of the reference antibody comprises LCDR1, LCDR2 and LCDR3, the LCDR1 comprises an amino acid sequence as shown in SEQ ID NO:1; the LCDR2 comprises an amino acid sequence as shown in SEQ ID NO:2; the LCDR3 comprises an amino acid sequence as shown in SEQ ID NO:3, the heavy chain variable region of the reference antibody comprises HCDR1, HCDR2 and HCDR3, the HCDR1 comprises an amino acid sequence as shown in SEQ ID NO:4; the HCDR2 comprises an amino acid sequence as shown in SEQ ID NO:5; and the HCDR3 comprises an amino acid sequence as shown in SEQ ID NO:6.

13. The antibody or the antigen-binding fragment thereof according to embodiment 12, wherein the light chain variable region of the reference antibody comprises an amino acid sequence as shown in SEQ ID NO:7, and the heavy chain variable region of the reference antibody comprises an amino acid sequence as shown in SEQ ID NO:8.

14. The antibody or the antigen-binding fragment thereof according to any one of embodiments 12-13, wherein the light chain of the reference antibody comprises an amino acid sequence as shown in SEQ ID NO:22; and the heavy chain of the reference antibody comprises an amino acid sequence as shown in SEQ ID NO:23.

15. The antibody or the antigen-binding fragment thereof according to any one of embodiments 1-14, which competes with a reference antibody to bind to the CD38 protein, wherein the reference antibody comprises a light chain and a heavy chain, wherein the light chain of the reference antibody comprises an amino acid sequence as shown in any one of SEQ ID NO:11, SEQ ID NO:16, SEQ ID NO:18 and SEQ ID NO:20; and the heavy chain of the reference antibody comprises an amino acid sequence as shown in any one of SEQ ID NO:13, SEQ ID NO:17, SEQ ID NO:19 and SEQ ID NO:21.

16. The antibody or the antigen-binding fragment thereof according to any one of embodiments 1-15, wherein the antibody comprises the light chain of the antibody or the fragment thereof.

17. The antibody or the antigen-binding fragment thereof according to embodiment 16, wherein the light chain of the antibody or the fragment thereof comprises LCDR1, and the LCDR1 comprises an amino acid sequence as shown in SEQ ID NO:1.

18. The antibody or the antigen-binding fragment thereof according to any one of embodiments 16-17, wherein the light chain of the antibody or the fragment thereof comprises LCDR2, and the LCDR2 comprises an amino acid sequence as shown in SEQ ID NO:2.

19. The antibody or the antigen-binding fragment thereof according to any one of embodiments 16-18, wherein the light chain of the antibody or the fragment thereof comprises LCDR3, and the LCDR3 comprises an amino acid sequence as shown in SEQ ID NO:3.

20. The antibody or the antigen-binding fragment thereof according to any one of embodiments 16-19, wherein the light chain of the antibody or the fragment thereof comprises a light chain variable region VL, and the light chain variable region VL comprises an amino acid sequence as shown in SEQ ID NO:7.

21. The antibody or the antigen-binding fragment thereof according to any one of embodiments 16-20, wherein the light chain of antibody or a fragment thereof further comprises human constant region.

22. The antibody or the antigen-binding fragment thereof according to embodiment 21, wherein the human constant region comprises a human Igκ constant region.

23. The antibody or the antigen-binding fragment thereof according to any one of embodiments 16-22, wherein the light chain of the antibody or the fragment thereof comprises an amino acid sequence as shown in SEQ ID NO:22.

24. The antibody or the antigen-binding fragment thereof according to embodiment 27, wherein the light chain of the antibody or the fragment thereof comprises an amino acid sequence as shown in any one of SEQ ID NO:11, SEQ ID NO:16, SEQ ID NO:18 and SEQ ID NO:20.

25. The antibody or the antigen-binding fragment thereof according to any one of embodiments 1-24, wherein the antibody comprises a heavy chain of the antibody or a fragment thereof.

26. The antibody or the antigen-binding fragment thereof according to embodiment 25, wherein the heavy chain of the antibody or the fragment thereof comprises HCDR1, and the HCDR1 comprises an amino acid sequence as shown in SEQ ID NO:4.

27. The antibody or the antigen-binding fragment thereof according to any one of embodiments 25-26, wherein the heavy chain of the antibody or the fragment thereof comprises HCDR2, and the HCDR2 comprises an amino acid sequence as shown in SEQ ID NO:5.

28. The antibody or the antigen-binding fragment thereof according to any one of embodiments 25-27, wherein the heavy chain of the antibody or the fragment thereof comprises HCDR3, and the HCDR3 comprises an amino acid sequence as shown in SEQ ID NO:6.

29. The antibody or the antigen-binding fragment thereof according to any one of embodiments 25-28, wherein, the heavy chain of the antibody or the fragment thereof comprises a heavy chain variable region VH, and the heavy chain variable region VH comprises an amino acid sequence as shown in SEQ ID NO:8.

30. The antibody or the antigen-binding fragment thereof according to any one of embodiments 25-29, wherein the heavy chain of the antibody or the fragment thereof further comprises a human constant region.

31. The antibody or the antigen-binding fragment thereof according to embodiment 30, wherein the human constant region comprises a human IgG constant region.

32. The antibody or the antigen-binding fragment thereof according to embodiment 31, wherein the IgG constant region comprises a human IgG1 constant region.

33. The antibody or the antigen-binding fragment thereof according to any one of embodiments 25-32, wherein, the heavy chain of the antibody comprises an amino acid sequence as shown in SEQ ID NO:23.

34. The antibody or the antigen-binding fragment thereof according to embodiment 33, wherein the heavy chain of the antibody comprises an amino acid sequence as shown in any one of SEQ ID NO:13, SEQ ID NO:17, SEQ ID NO:19 and SEQ ID NO:21.

35. One or more isolated nucleic acid molecules, comprising a polynucleotide encoding the antibody or the antigen-binding fragment thereof according to any one of embodiments 1-34.

36. The nucleic acid molecule according to embodiment 35, wherein at least one of the nucleic acid molecules is codon optimized.

37. The nucleic acid molecule according to any one of embodiments 35-36, wherein the nucleic acid molecule comprises one or more polynucleotide sequences selected from the group comprising SEQ ID NO:9, SEQ ID NO:10, SEQ ID NO:12 and SEQ ID NO:14.

38. A vector, comprising the nucleic acid molecule according to any one of embodiments 35-37.

39. A cell, comprising the nucleic acid molecule according to any one of embodiments 35-37 or the vector according to embodiment 38.

40. A method for preparing the antibody or the antigen-binding fragment thereof according to any one of embodiments 1-34, comprising culturing the cell according to embodiment 39 under conditions that allow to express the antibody or the antigen-binding fragment thereof.

41. A pharmaceutical composition, comprising the antibody or the antigen-binding fragment thereof according to any one of embodiments 1-34, the nucleic acid molecule according to any one of embodiments 35-37, the vector according to embodiment 38, or the cell according to embodiment 39, and an optionally pharmaceutically acceptable adjuvant.

42. An application of the antibody or the antigen-binding fragment thereof according to any one of embodiments 1-34 in preparation of medicaments for preventing or treating tumors.

43. The application according to embodiment 42, wherein the tumors comprise a CD38 positive tumor.

44. The application according to embodiment 43, wherein the CD38 positive tumor is selected from the group comprising multiple myeloma, lymphoma and leukemia.

45. The application according to embodiments 42-44, wherein the tumor is selected from the group comprising non-Hodgkin lymphoma and Hodgkin's lymphoma.

46. An antibody or the antigen-binding fragment thereof according to any one of embodiments 1-34 for preventing or treating tumors.

47. The antibody or the antigen-binding fragment thereof according to embodiment 46, wherein the tumors comprise a CD38 positive tumor.

48. The antibody or the antigen-binding fragment thereof according to embodiment 47, wherein the CD38 positive tumor is selected from the group comprising multiple myeloma, lymphoma and leukemia.

49. The application according to any one of embodiments 46-48, wherein the tumor is selected from the group comprising non-Hodgkin lymphoma and Hodgkin's lymphoma.

50. A method for preventing or treating tumors in a subject in need thereof, comprising administering to the subject the antibody or the antigen-binding fragment thereof according to any one of embodiments 1-34, the nucleic acid molecule according to any one of embodiments 35-37, the vector according to embodiment 38, the cell according to embodiment 39, and/or the pharmaceutical composition according to embodiment 40.

51. The method according to embodiment 50, wherein the tumors comprise a CD38 positive tumor.

52. The method according to embodiment 51, wherein the CD38 positive tumor is selected from the group comprising multiple myeloma, lymphoma and leukemia.

53. The method according to any one of embodiments 50-52, wherein the tumor is selected from the group comprising non-Hodgkin lymphoma and Hodgkin's lymphoma.

54. A method for inhibiting the binding of a CD38 protein to a CD38 ligand, comprising administering the antibody or the antigen-binding fragment thereof according to any one of embodiments 1-34, the nucleic acid molecule according to any one of embodiments 35-37, the vector according to embodiment 38, and/or the cell according to embodiment 39.

55. The method according to embodiment 54, wherein the CD38 ligand comprises CD31.

Without wishing to be bound by any theory, the following examples are only for explaining the working mode of the products, methods, or systems of the present application, but not intended to limit the scope of the invention of the present application.

EXAMPLES

Example 1: Preparation of Hybridoma Antibody and Gene Cloning

Immunization of mice: balb/c mice (purchased from Beijing Vital River Labs Animal Technology Co., Ltd.) were subcutaneously (s.c.) immunized for 3 times with Freund's adjuvant or Freund's incomplete adjuvant mixed with 100 λg of soluble CD38 antigen (purchased from Beijing Yiqiao Shenzhou Biotechnology Co., Ltd.). On Day 0, the Freund's complete adjuvant was used, and on Day 14 and Day 28, the Freund's incomplete adjuvant was used. Spleen cells of the immunized mice were fused to the mouse myeloma cells SP2/0 (ATCC) according to a standard method.

Hybridoma fusion: the mouse spleens were fused according to the current conventional hybridoma fusion method, and the fused hybridoma cells ($10^5$ cells per well) were screened according to the HAT screening method. After 12 days, the supernatant was subject to ELISA assay with a microplate coated with CD38 antigen. The preferred clones are subject to the second round of subcloning by limiting dilution analysis. The obtained hybridoma strain that stably expresses the antibody of interest was subject to seed preservation and library construction.

RNA preparation: RNA was prepared by using an RNA extraction kit TRIzol Reagent (purchased from Life technologies). A reverse transcription kit (purchased from Beijing Quanshijin Biotechnology Co., Ltd.) was used to prepare the cDNA encoding the antibody gene, and the cDNA was used as a template for the PCR amplification of the antibody variable region gene. The T-easy vector was cloned, and the obtained heavy chain and light chain variable region sequences after cloning were sequenced, so as to further obtain the corresponding amino acid sequences.

Example 2: Humanization and Preparation of Antibody

The heavy and light chain sequences of the murine antibody variable regions obtained in Example 1 were subject to sequence alignment with the existing human antibody sequences in the NCBI database via the online sequence alignment method (IgBlast) provided by NCBI, to determine the potential humanized sites. Further, a three-dimensional structure of the murine antibody variable region was constructed via SwissModel, to determine the humanized sites. With respect to the corresponding humanized sites, humanization was carried out to obtain the humanized antibody sequence.

The humanized antibody was named SG003, and the sequencing results showed that the amino acid sequences of LCDR1-3 of the antibody SG003 are shown in SEQ ID NO.1, SEQ ID NO.2, and SEQ ID NO.3, respectively; the amino acid sequence of VL is shown in SEQ ID NO.7; the nucleotide sequence encoding VL obtained by codon optimization and reverse translation is shown in SEQ ID NO.9; the amino acid sequences of HCDR1-3 of the antibody SG003 are shown in SEQ ID NO.4, SEQ ID NO.5 and SEQ ID NO.6, respectively; the amino acid sequence of VH is shown in SEQ ID NO.8; and the nucleotide sequence encoding VH obtained by codon optimization and reverse translation is shown in SEQ ID NO.10.

The amino acid sequence of the light chain of the antibody SG003 is shown in SEQ ID NO.11; and the nucleotide sequence encoding therefor is shown in SEQ ID NO.12. The amino acid sequence of the heavy chain of the antibody SG003 is shown in SEQ ID NO.13; and the nucleotide sequence encoding therefor is shown in SEQ ID NO.14.

The obtained humanized antibody variable region genes were cloned into a eukaryotic expression vector pCMV-163 containing the human IgG constant region gene, to construct a full antibody expression vector with a physical map as shown in FIG. 1. In FIG. 1, various components of the eukaryotic expression vector pCMV-163 are known in the art and recombined in the order as shown.

An ExpiCHO™ Expression System kit (purchased from Thermo Fisher Scientific) was used to transfect the obtained eukaryotic expression vector encoding the antibody SG003 into CHO-S cells for expression, and the cell culture supernatant containing the protein of interest was collected. The target antibody was purified by using the conventional protein A affinity purification.

Example 3: Binding of Humanized Antibody to Target Antigen

Figure 2:
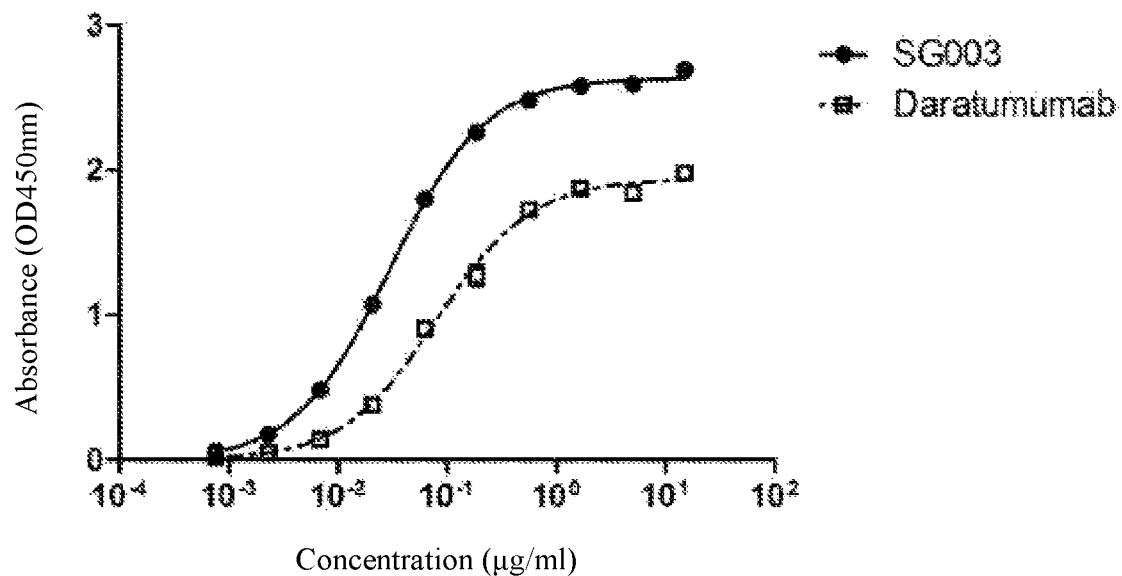
FIG. 2 shows the binding ability of the antibody SG003 of the present application to a CD38 protein.

An ELISA plate was coated with a PBS solution containing 1 µg/ml of CD38-His fusion protein at 4° C. overnight. The plate was then washed with a PBS solution containing 0.01% Tween-20 (PBST). 10% fetal bovine serum was added to the PBST and blocked at 37° C. for 1 hour. Then, different concentrations of the SG003 antibody and a control antibody Daratumumab (DARZALEX) were added and reacted at 37° C. for 1 hour. After washing with PBST, horseradish peroxidase-labeled goat anti-human IgG HRP secondary antibodies (purchased from Thermo Fisher Scientific) was added and reacted at 37° C. for 30 minutes. Then, the plate was washed with PBST (5 times), and the residual liquid drops were removed as possible on an absorbent paper. 100 µl of TMB (purchased from eBioscience) was added to each well, and placed at room temperature (20±5° C.) in the dark for 1-5 minutes. 100 µl of 2N H2SO4 stop solution was added to each well to quench the substrate reaction. The OD value was read at 450 nm with a microplate reader, and the binding ability of the antibody to the target antigen CD38-His was analyzed. The results show that the SG003 antibody showed a stronger binding activity than the control antibody Daratumumab, and the results are shown in FIG. 2. In FIG. 2, the EC50 value is 35.1±10.5 ng/mL, while the EC50 value of the Daratumumab antibody is 150.9±105.8 ng/mL.

Example 4: Determination of Affinity of Humanized Antibody

The antibody affinity was analyzed by BIACORE Biomacromolecule Interaction Apparatus (GE). The anti-human IgG-Fab antibody (purchased from Abcam) was coupled to the chip, and anti-human IgG antibody was used to capture SG003 antibody. The concentration of the antibody was set at 1 g/mL, the injection time was 60-150 seconds; the antigen CD38 was used as the mobile phase; 6 concentration gradients (3.125, 6.25, 12.5, 25, 50, 100 nM) were used, the association time was 120 seconds; the dissociation time was 1200 seconds; 10 mM glycine-hydrochloric acid buffer (pH 2.1) was used for regeneration for 60 seconds. The results show that the SG003 antibody affinity was as shown in Table 1.

TABLE 1

| Affinity of SG003 Antibody | | | |
|---|---|---|---|
| Antibody | Association Constant ($10^6$ 1/Ms) | Dissociation Constant ($10^{-4}$ 1/s) | Relative Affinity ($10^{-10}$ M) |
| SG003 | 2.86 ± 0.00 | 9.18 ± 0.01 | 3.21 ± 0.01 |

Example 5: Specific Recognition of Humanized Antibody on Target Antigen

Various proteins, such as milk (Beijing Bomed Biotechnology Co., Ltd.), BSA (BOVOGEN), CD19 (Beijing Yiqiao Shenzhou Biotechnology Co., Ltd.), TROP2 (Beijing Yiqiao Shenzhou Biotechnology Co., Ltd.), CD47 (Beijing Magpel Biotech Technology Co., Ltd.), CD38 (Beijing Yiqiao Shenzhou Biotechnology Co., Ltd.), Gas6 (R&D) and AXL (ACRO Biosystems) were respectively used to coat ELISA strips at 1 mg/ml at 4° C. overnight. After washing with PBST, 10% fetal bovine serum was added and blocked at 37° C. for 1 hour. The SG003 antibody was added and reacted at 37° C. for 1 hour. After washing with PBST, horseradish peroxidase-labeled goat anti-human IgG HRP secondary antibodies (purchased from ThermoFisher Scientific) was added and reacted at room temperature for 30 minutes. After washing the plate with PBST (5 times), the residual drops were removed as possible on the absorbent paper. 100 ml TMB (eBioscience) was added to each well and placed at room temperature (20±5° C.) in the dark for 1-5 min. 100 ml of 2N H2SO4 stop solution was added to each well to quench the substrate reaction, and the OD value was read at 450 nm with a microplate reader to analyze the antibody-protein binding ability.

Figure 3:
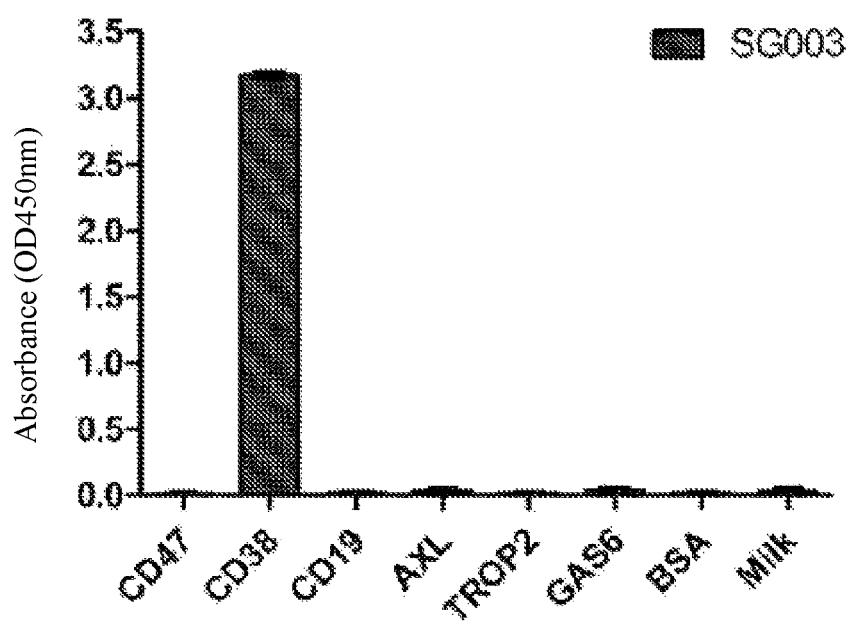
FIG. 3 shows the results of the specific recognition of CD38 protein by the antibody SG003 of the present application.

The results are shown in FIG. 3. The results in FIG. 3 show that the SG003 antibody can specifically recognize the target antigen CD38, but has no significant binding reaction with milk, BSA, CD19, TROP2, CD47, AXL, Gas6 and other proteins.

Example 6: Binding of Humanized Antibody to Antigen on Cell Surface

The flow analysis technology was used to detect the binding of CD38 proteins on the surfaces of Raji cells, Daudi cells, Ramos cells and RPMI8226 cells to the SG003 antibody and the control antibody Daratumumab. The logarithmic growth phase cells were collected, adjusted to a cell density of $5\times10^6$ cells/mL, and pre-cooled on ice. The SG003 antibody and the control antibody Daratumumab were diluted to different concentrations with pre-cooled normal saline containing 2% FBS. 100 µL of cells were taken, and an equal volume of the diluted antibody was added for reaction at 4° C. for 30 min in the dark. After the completion of reaction, the cells were washed twice. The cells were resuspended in 100 µL of the diluted PE Mouse Anti-Human IgG secondary antibodies (purchased from BD Pharmingen), and reacted at 4° C. in the dark for 30 min. After the completion of reaction, the cells were washed twice with a pre-cooled normal saline containing 2% FBS. The cells were resuspended in 400 µL of 1% paraformaldehyde. Flow cytometry (BD Calibur) was used to analyze the binding ability of antibodies to cell surface antigens.

Figure 4A:
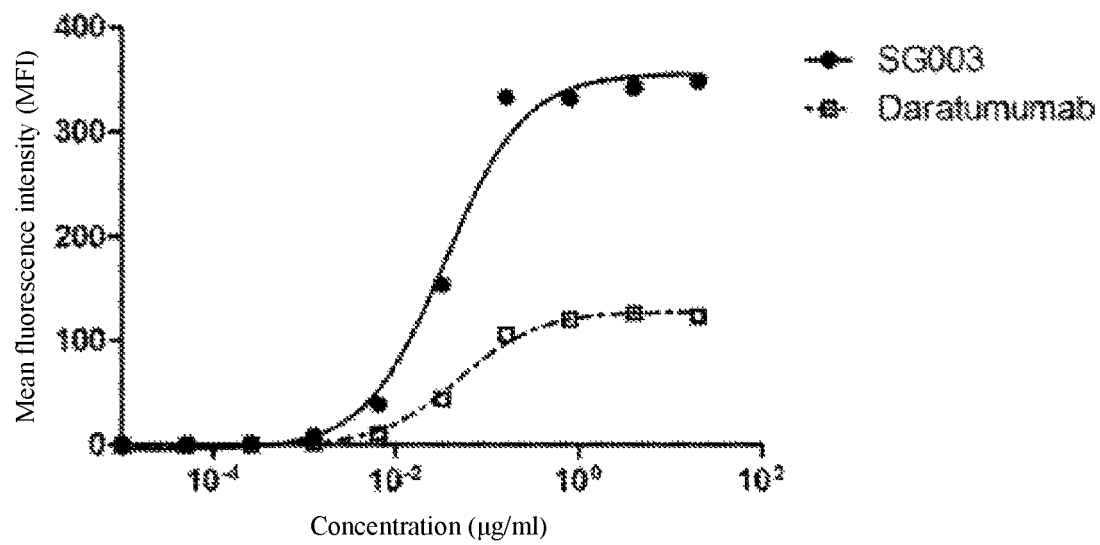
FIGS. 4A-4D show the binding ability of the antibody SG003 of the present application to the CD38 protein on the surface of representative cells.
Figure 4B:
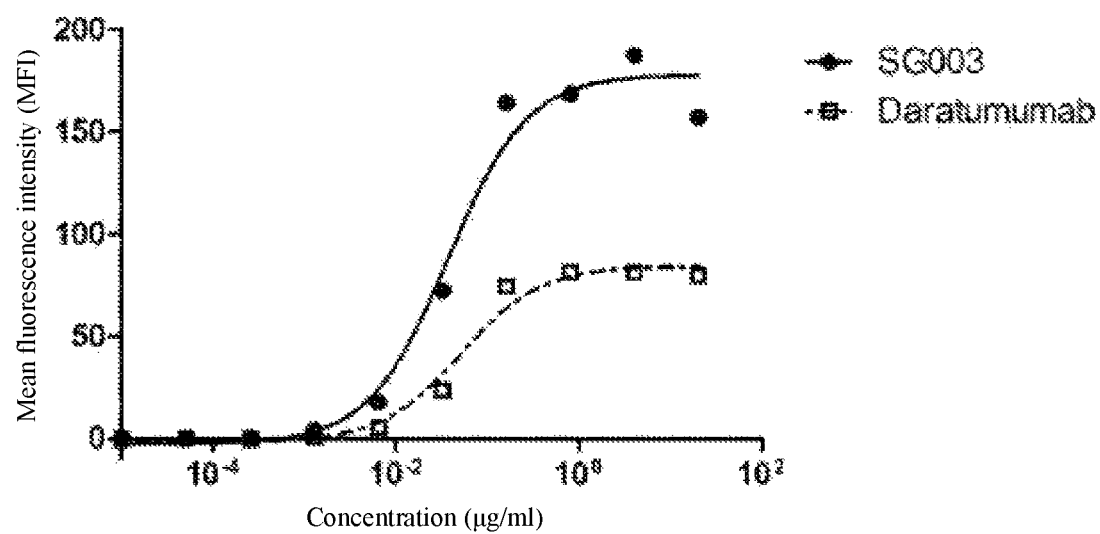
Figure 4C:
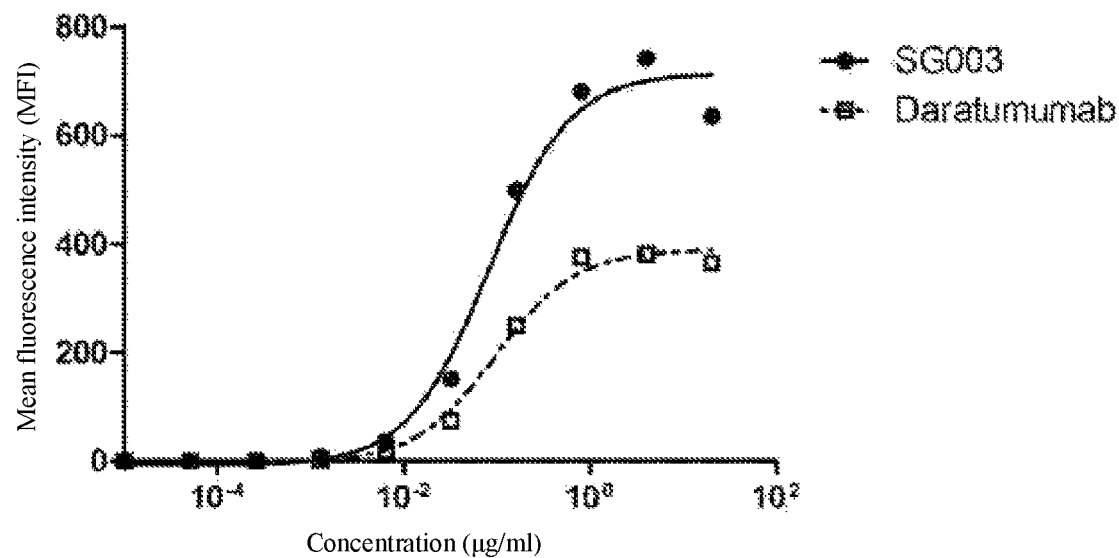
Figure 4D:
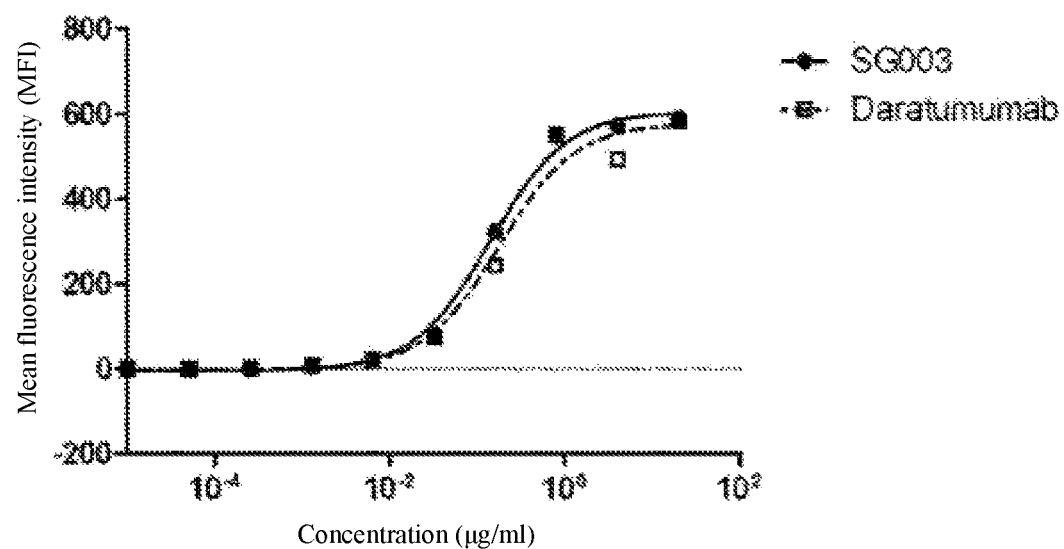

The results show that the SG003 antibody can specifically recognize the CD38 on the surfaces of Raji cells, Daudi cells, Ramos cells and RPMI8226 cells. This recognition activity is significantly higher than that of the control antibody Daratumumab in a dose-dependent manner, and the EC50 value of SG003 combined with Raji cells (FIG. 4A) was 34.4 ng/mL, and Daratumumab was 49.3 ng/mL. The EC50 value of SG003 combined with Daudi cells (FIG. 4B) was 36.7 ng/mL, and Daratumumab was 50.9 ng/mL. The EC50 value of SG003 combined with Ramos cells (FIG. 4C) was 81.5 ng/mL, and Daratumumab was 95.1 ng/mL. The EC50 value of SG003 combined with RPMI8226 cells (FIG. 4D) was 140.3 ng/mL, and Daratumumab was 176.5 ng/mL.

Example 7: Antibody-Dependent Cell-Mediated Cytotoxicity (ADCC) Activity of Humanized Antibody First, the target cells (Raji cells, Daudi cells, Ramos cells and RPMI8226 cells) required for the experiment were adjusted to a density of $2\times10^5$ cells/mL, resuspended in an ADCC buffer (phenol red-free MEM medium+1% FBS), and added to a 96-well plate (50 μL/well). Then, 100 μL of SG003 antibody of different concentrations was added to each well, mixed homogeneously and incubated at 37° C. in an incubator containing 5% $CO_2$ for 30 minutes. Then, the required effector cells NK92MI-CD16a (purchased from Huabo Bio) were adjusted to a density of $1.2\times10^6$ cell/mL, and added to the wells with the target cells, such that a ratio of target cells to effector cells was equal to 1:6. After mixing, the mixture was incubated at 37° C. for 4-6 h in an incubator containing 5% $CO_2$, and then a portion of the stock solution (100 μL/well) in the 96-well plate was removed and the LDH reaction mixture in an LDH detection kit (Cytotoxicity Detection Kit, purchased from Roche) (100 μL/well) was added into each well. The mixture was reacted at 37° C. for 10 min. Then, a stop solution (50 μL/well) was added and mixed gently. The OD value was read at 492 nm with a microplate reader, and the OD value at 650 nm was used as the background value. In the experiment, the following control groups were also set: wherein, control 1 was ADCC buffer, control 2 was target cells+ADCC buffer, control 3 was target cells+lysate+ADCC buffer, and control 4 was target cells+effector cells+ADCC buffer liquid. Specific killing rate %=((Experimental group−Control 4)/(Control 3−Control 2))×100%. The dose-effect curve was subject to data analysis by GraphPad Prism Version 5.

Figure 5A:
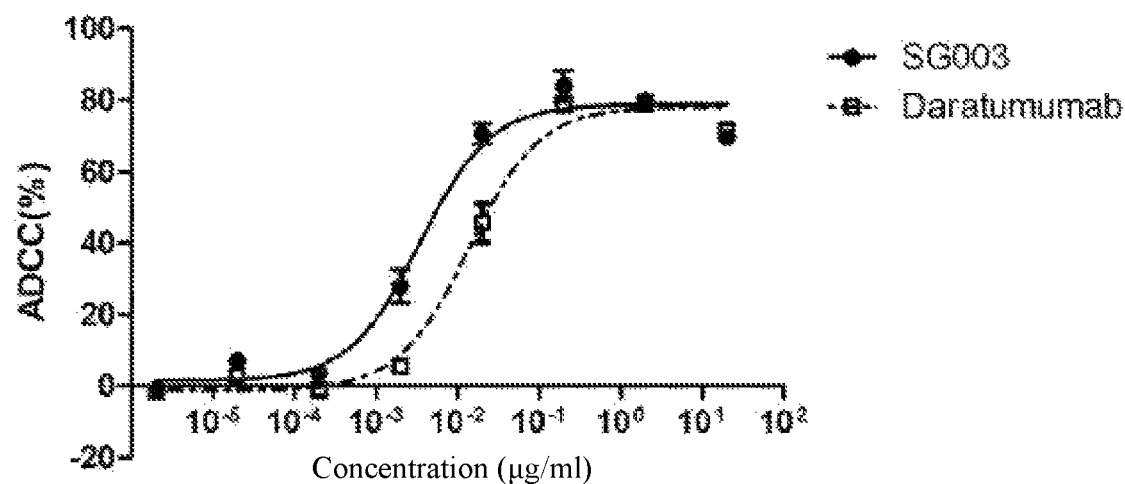
FIGS. 5A-5D show the ADCC activity of the antibody SG003 of the present application on representative cells.
Figure 5B:
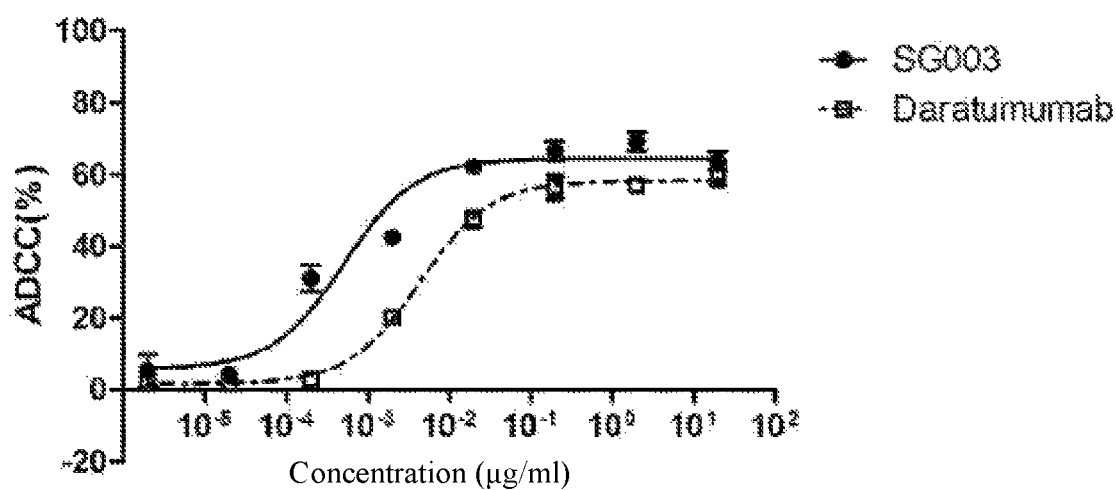
Figure 5C:
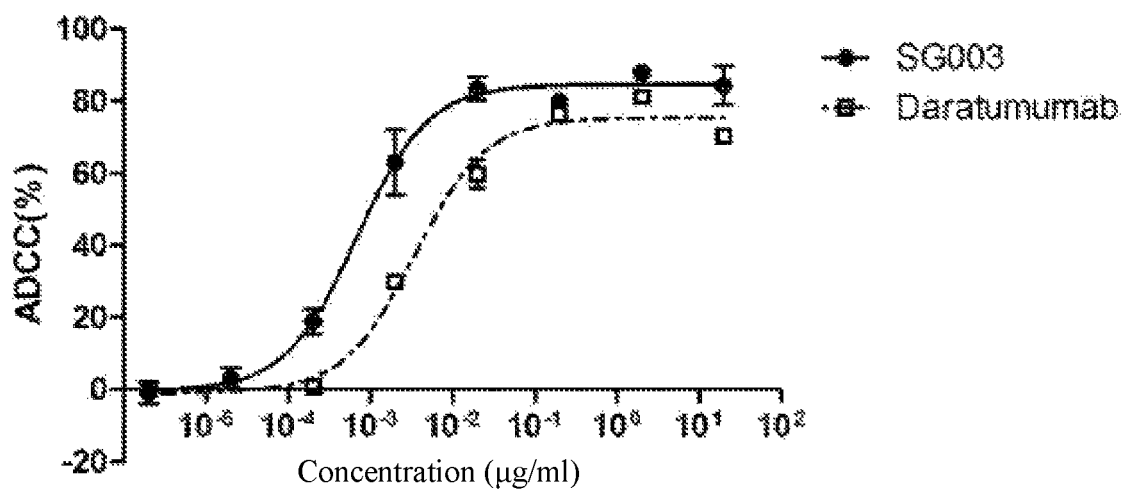
Figure 5D:
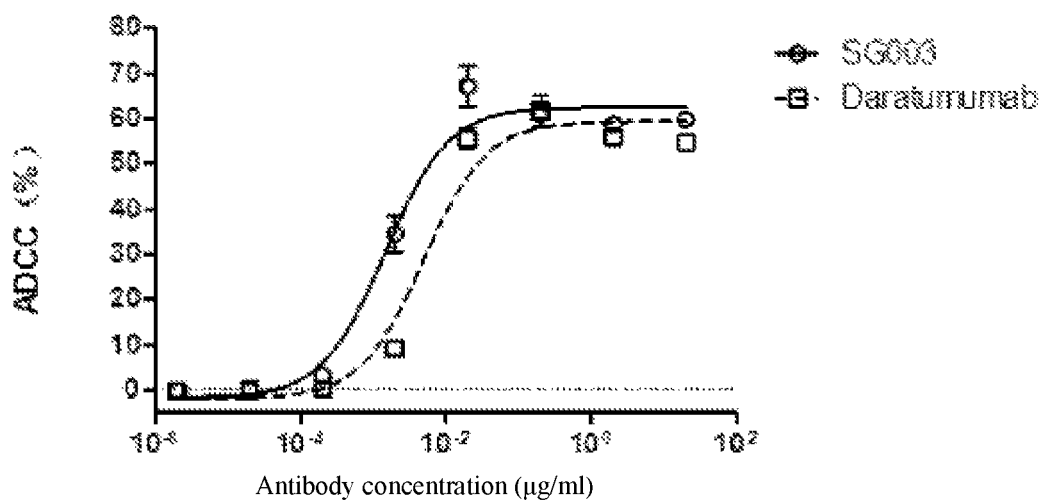

The results show that when tested with Raji target cells and NK92MI-CD16a effector cells, the SG003 antibody showed a very effective ADCC activity (see FIG. 5A), with an EC50 value of SG003 was 6.97 ng/mL and Daratumumab was 17.0 ng/mL. When Daudi is used as a target cell, the EC50 value of SG003 was 0.72 ng/mL, and Daratumumab was 4.6 ng/mL (refer to FIG. 5B). At the same time, the SG003 antibody also showed an effective ADCC activity on Ramos cells (refer to FIG. 5C). The EC50 value of SG003 was 0.69±0.007 ng/mL, and Daratumumab was 3.01 ng/mL. The SG003 antibody also showed an effective ADCC activity against RPMI8226 cells (refer to FIG. 5D), with an EC50 value of SG003 of 1.46 ng/mL and Daratumumab of 4.94 ng/mL.

Example 8: In Vivo Inhibition of Humanized Antibody on Tumor Activity

The tumor model was established by inoculating Raji-Luc cells into CB17 SCID mice, to evaluate the effect of SG003 antibody in inhibiting tumor activity.

Female, 5-8-week-old CB17 SCID mice (purchased from Beijing Biocytogen Co., Ltd.) were selected for the experiment. Raji-Luc cell is a stable cell line obtained by Beijing Biocytogen Co., Ltd. on the basis of Raji cell, which is transformed with luciferin reporter gene. After resuscitating and cultivating to the required number, logarithmic phase growth cells were collected and suspended to a concentration of $5\times10^6$ cells/0.2 mL. The CB17 SCID mice were inoculated through the tail vein in the amount of 0.2 mL/mouse. After inoculation, the mice were observed with a small animal imager for the tumor growth and body weight on Day 0 and Day 7. On Day 7, 18 mice with moderate tumor imaging signals were selected, and randomly assigned to 3 groups, 6 in each group. Then, the animals began to be administered. A saline control group, a positive control group (Daratumumab, purchased from Johnson & Johnson) and an experimental group (SG003) were set, and the dosage was 200 μg/kg, once every two weeks, a total of twice. Next, the mice were observed for the body weight, tumor growth and survival rate.

Figure 6:
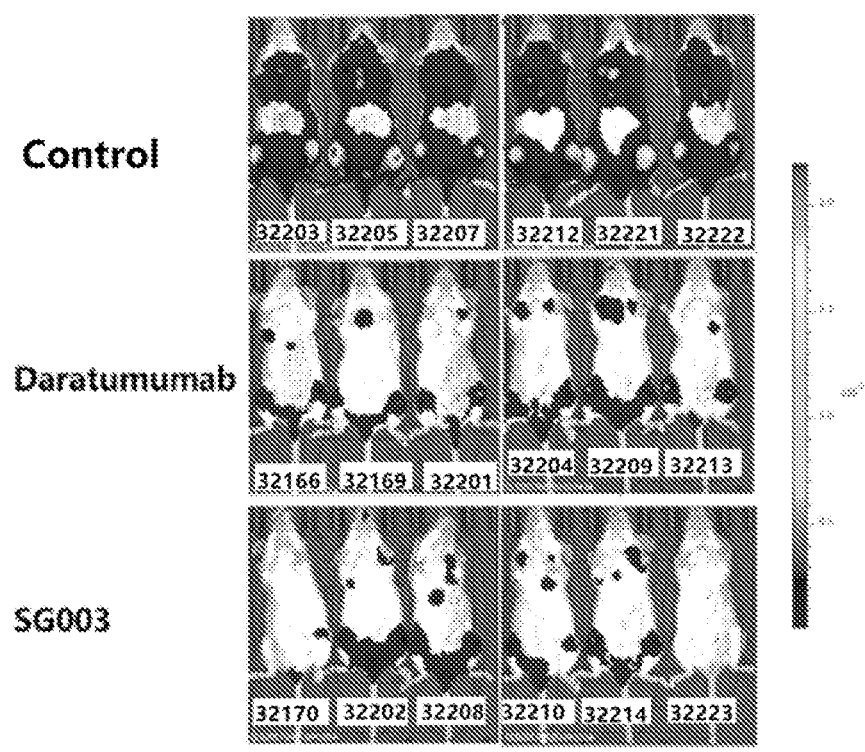
FIG. 6 shows the inhibitory effect of the antibody SG003 of the present application on tumor growth.

The results show that both Daratumumab and SG003 antibodies can be tolerated by experimental animals. The animals administered in each group had a significant tumor growth inhibitory effect compared with the solvent control group (refer to FIG. 6). On Day 7 after the first administration, the average fluorescence intensity of Daratumumab and SG003 antibody treatment groups were respectively (average 3.92E+07, standard error 4.04E+06), (average 3.19E+07, standard error: 9.32E+06), significantly lower than the average tumor fluorescence intensity of the control group (average 3.04E+08, standard error 4.29E+07).

Figure 7:
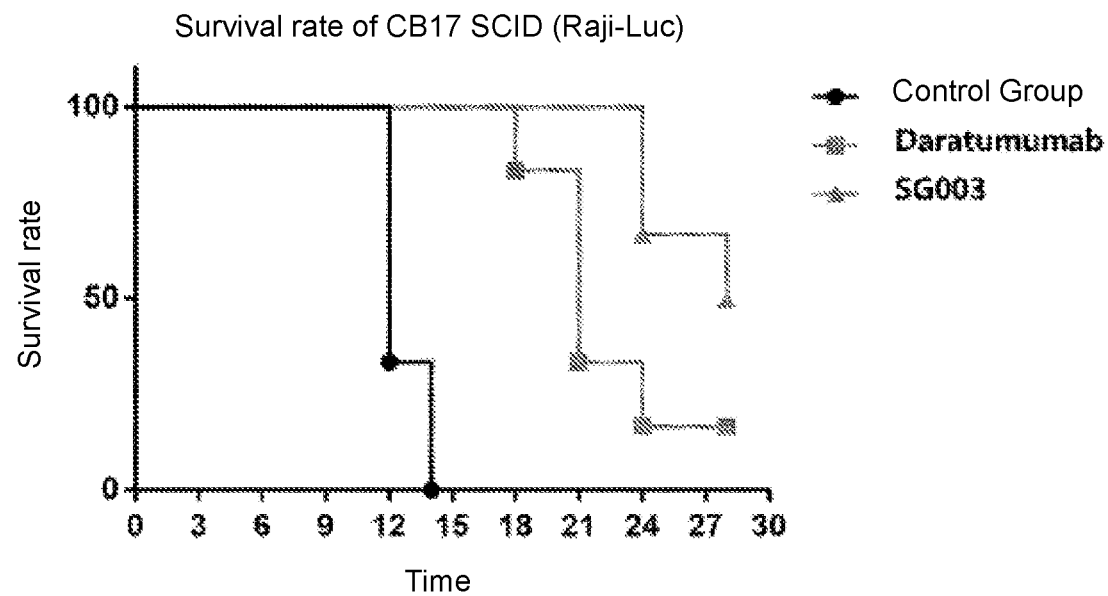
FIG. 7 shows the effect of the administration of the antibody SG003 of the present application on the survival rate of mice.

Then, the animal survival rate was further observed. The median survival time of the control group was 12 days after grouping, Daratumumab was 21 days, and SG003 group was 28 days. The SG003 group is superior to the Daratumumab group (refer to FIG. 7).

Example 9: Species Recognition Specificity of Chimeric Antibody

The CD38 extracellular proteins (Beijing Yiqiao Shenzhou Biotechnology Co., Ltd.) of different species of human (Human), mouse (Mouse), rat (Rat), cynomolgus monkey (Cynomolgus) and the like were respectively used to coat ELISA strips at 1 mg/ml at 4° C. overnight. After washing with PBST, 10% fetal bovine serum was added and blocked at 37° C. for 1 hour. The to-be-tested SG003 antibody and the control antibody Daratumumab were added, respectively, and reacted at 37° C. for 1 hour. After washing with PBST, horseradish peroxidase-labeled goat anti-human IgG HRP secondary antibodies (purchased from Thermo Fisher Scientific) was added and reacted at room temperature for 30 minutes. The plate was washed with PBST (5 times), and the remaining drops were removed as possible on the absorbent paper. 100 ml of TMB (purchased from eBioscience) was added to each well, and placed at room temperature (20±5° C.) in the dark for 1-5 min. 100 ml of 2N $H_2SO_4$ stop solution was added to each well to quench the substrate reaction, and the OD value was read at 450 nm with a microplate, to analyze the binding ability of the antibody to CD38 protein of different species.

Figure 8A:
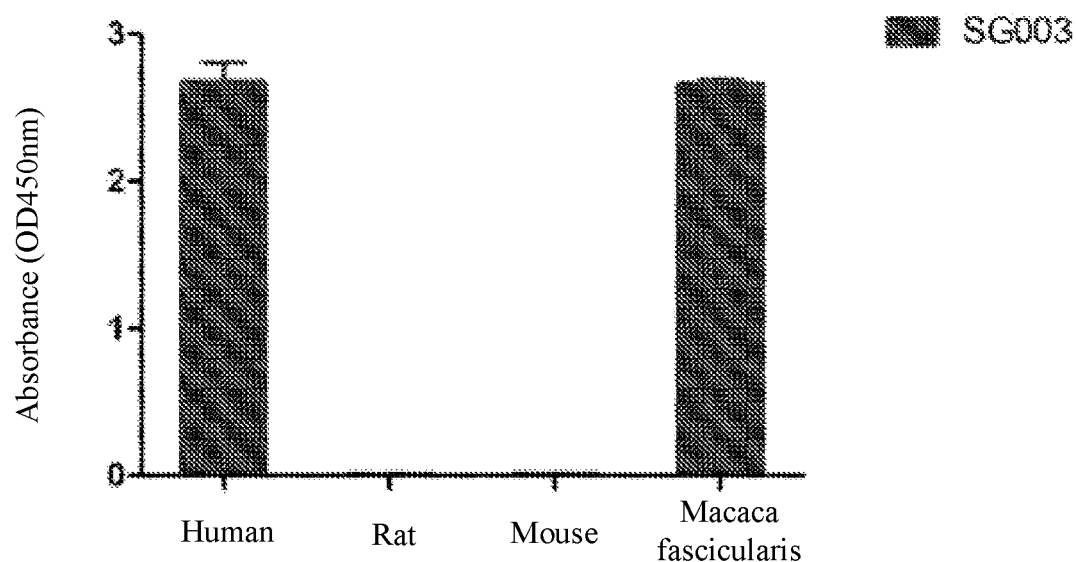
FIGS. 8A-8B show the binding ability of the administration of the antibody SG003 of the present application to CD38 molecules originated from different genera.

The results show that the SG003 antibody can recognize the CD38 protein molecules of human and cynomolgus monkeys, but has no binding reaction with the CD38 protein molecules of mice and rats; the results are shown in FIG. 8A.

Figure 8B:
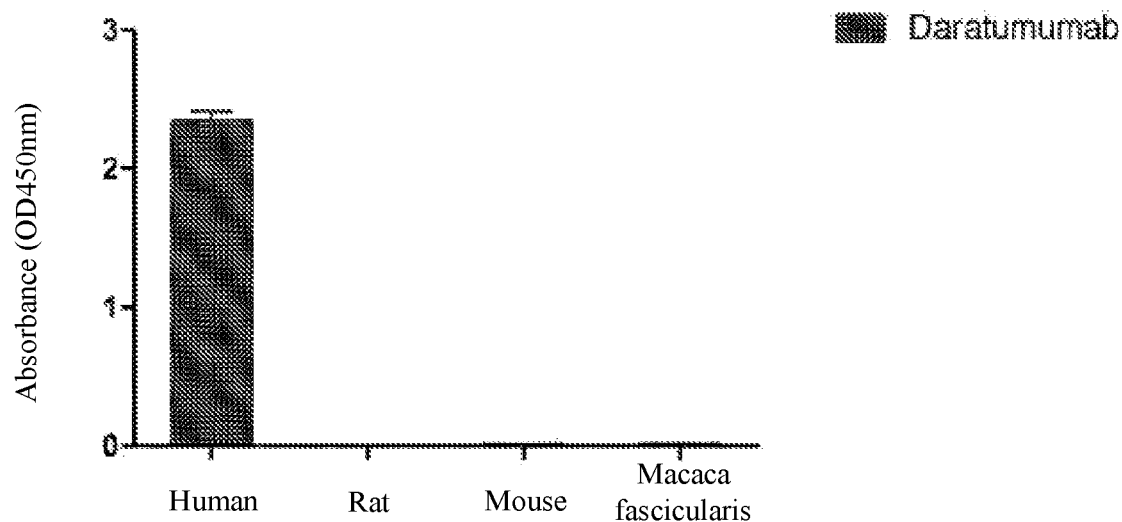

The control antibody Daratumumab only recognizes human CD38 protein molecules and has no binding reaction with the CD38 protein molecules of mice, rats and cynomolgus monkeys. The results are shown in FIG. 8B.

Example 10: Maintenance of Biological Activity of Humanized Antibody after Mutation With the aid of genetic engineering technology, the SG003 antibody variable region sequences can be randomly mutated to obtain new antibody variable region sequences, and further obtain new antibody light chain and heavy chain sequences. For example, for an antibody obtained after random mutation based on the SG003 antibody, the light chain amino acid sequence may be SEQ ID NO:16, and the heavy chain amino acid sequence may be SEQ ID NO:17; or, the light chain amino acid sequence may be SEQ ID NO:18, and the heavy chain amino acid sequence may be SEQ ID NO:19; alternatively, the light chain amino acid sequence may be SEQ ID NO:20, and the heavy chain amino acid sequence may be SEQ ID NO:21. The antibodies containing the above combination of the light chain and the heavy chain after the mutation are named SG03M1-3 in sequence (for example, the light chain amino acid sequence of the SG03M1 antibody is SEQ ID NO:16, and the heavy chain amino acid sequence is SEQ ID NO:17).

Figure 9:
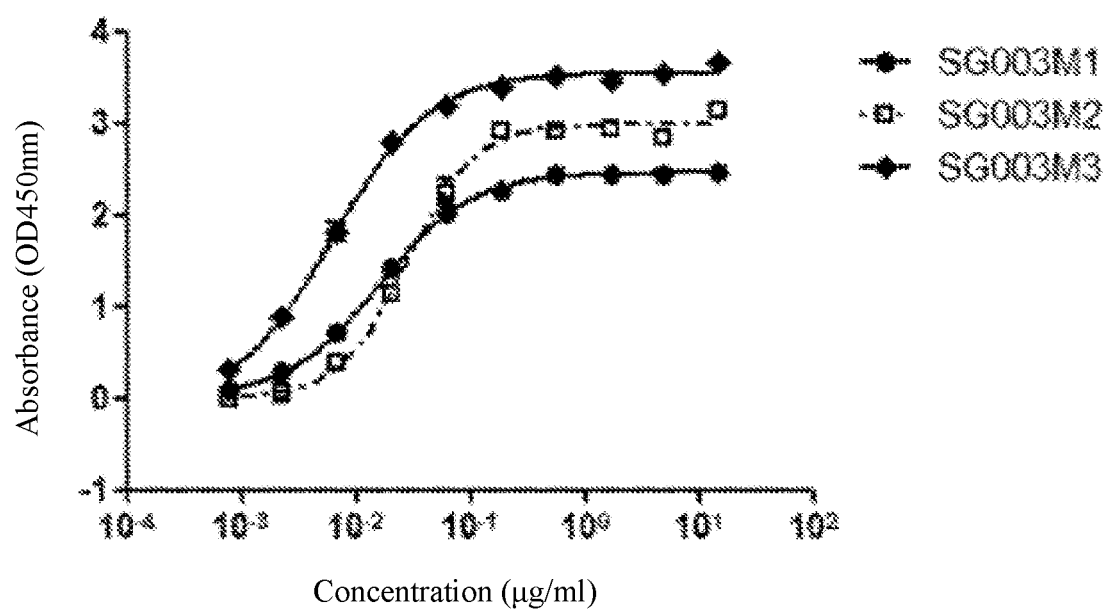
FIG. 9 shows the binding ability of the random-mutated antibody SG003 of the present application to CD38 molecules.

A new antibody was prepared by referring to the method of Example 2, and the antibody activity was evaluated by referring to the method of Example 4. The randomly mutated antibody SG003M1-3 can recognize the CD38 antigen (refer to FIG. 9). It was determined that the EC50 value of SG003M1 was 15.72 ng/mL, the EC50 value of SG003M2 was 27.75 ng/mL, and the EC50 value of SG003M3 was 6.10 ng/mL. Randomly select SG003M1 and determine the affinity results as shown in Table 2.

TABLE 2

Analysis of Affinity of SG003 Mutants

| Antibody | Association Constant ($10^6$ 1/Ms) | Dissociation Constant ($10^{-4}$ 1/s) | Affinity ($10^{-10}$ M) |
|---|---|---|---|
| SG003M1 | 2.66 ± 0.01 | 6.36 ± 0.05 | 2.39 ± 0.03 |

Example 11: Epitope Verification of Humanized Antibody

An epitope-mapping method was used to analyze the epitope of antibody SG003 which recognized CD38 antigen. CD38 antigen mutants (Table 3, wherein the mutated amino acids are all alanine) were designed by an alanine substitution method, and CD38 wild-type as well as various mutant genes were obtained by polymerase chain reaction (PCR) and overlap extension (overlap) and other molecular biology techniques. After separation and recovery by agarose gel electrophoresis, the antibody or mutants were digested with HindIII and NheI restriction enzymes, and cloned into a pEGFP-N1 vector. After correct sequencing, the HighGene Transfection Kit (ABclonal) was used to transfect the vector containing the CD38 wild-type or mutant gene into 293T cells according to the method described in the instructions of the kit. At 48 hours after transfection, cells were collected by trypsin digestion, to prepare a single-cell suspension. The target cells and antibody SG003 were incubated at a working concentration of 10 μg/ml for 30 minutes at a constant temperature of 4° C. Then, GAH-IgG Fc PE (Invitrogen, Cat: 12-4998-82) was added and incubated at a constant temperature of 4° C. for 30 minutes, and measured for the fluorescence intensity of FITC and PE channels by flow cytometry, wherein FITC fluorescence intensity represents the expression level of CD38 molecule and its mutants, and PE fluorescence intensity represents the strength of SG003 antibody binding antigen.

Figure 10:
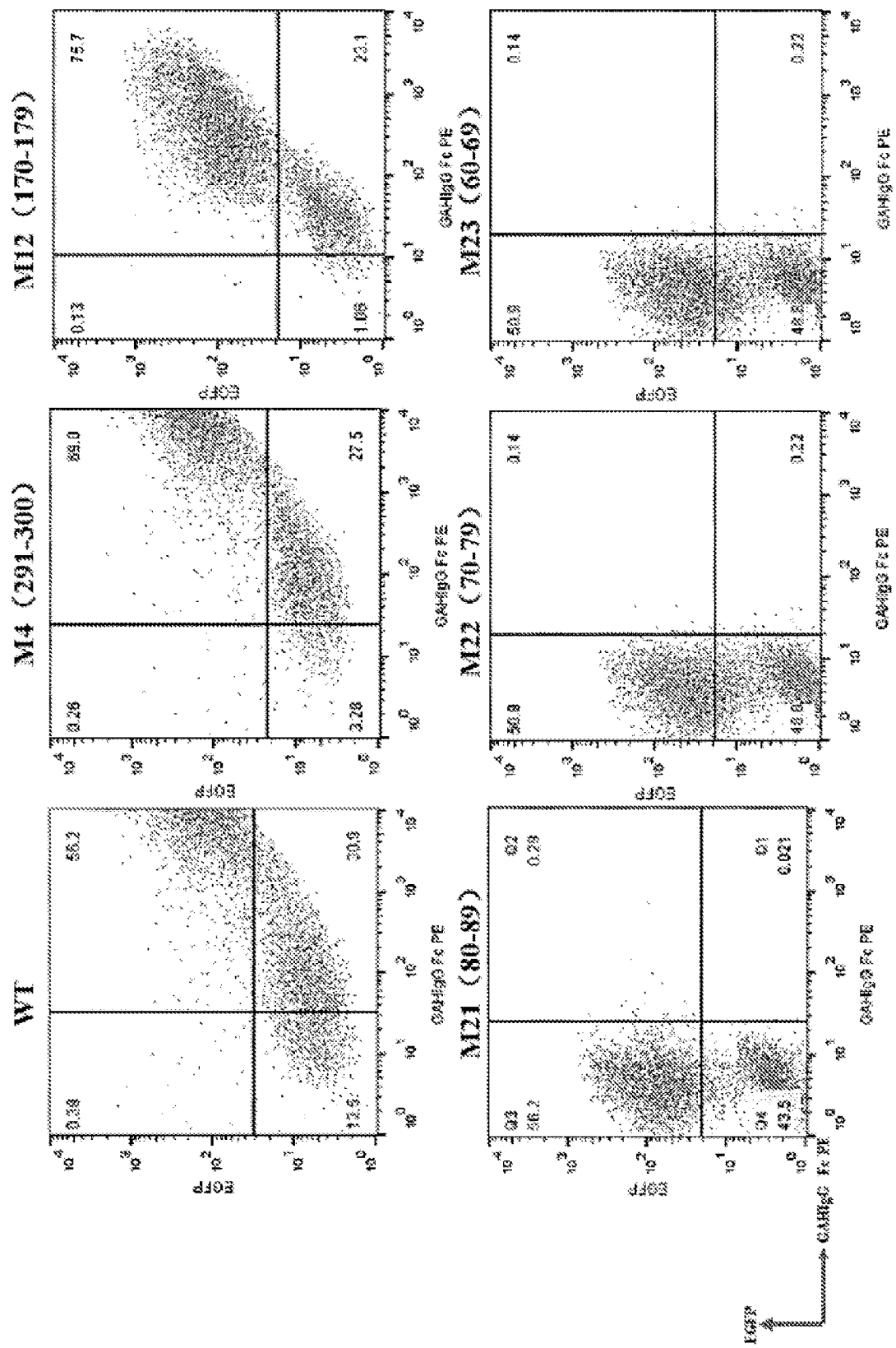
FIG. 10 shows the epitope circumstance of the antibody SG003 of the present application binding to the CD38 protein.

The flow cytometry results in FIG. 10 show that antibody SG003 does not bind to mutants 21, 22, and 23, which suggests that the amino acid region 60-89 of CD38 protein is the main epitope recognized by antibody SG003.

TABLE 3

Mutants and Mutation Sites of CD38 Protein

| Name | Mutation Site |
|---|---|
| CD38 Wild Type | N/A |
| CD38M4 | 291-300 |
| CD38M5 | 281-290 |
| CD38M6 | 256-266 |
| CD38M7 | 247-255 |
| CD38M8 | 210-219 |
| CD38M9 | 200-209 |
| CD38M10 | 190-199 |
| CD38M11 | 180-189 |
| CD38M12 | 170-179 |
| CD38M13 | 160-169 |
| CD38M14 | 150-159 |
| CD38M15 | 140-149 |
| CD38M16 | 130-139 |
| CD38M17 | 120-129 |
| CD38M18 | 110-119 |
| CD38M19 | 100-109 |
| CD38M20 | 90-99 |
| CD38M21 | 80-89 |
| CD38M22 | 70-79 |
| CD38M23 | 60-69 |
| CD38M24 | 50-59 |
| CD38M25 | 43-49 |

The foregoing detailed description is provided by way of explanation and example, and is not intended to limit the scope of the appended claims. Many variations of the embodiments as listed herein are obvious to those of ordinary skill in the art, and are within the scope of the appended claims and their equivalents.

The invention claimed is:

1. An antibody or an antigen-binding fragment thereof, which binds to a CD38 protein, comprising a light chain of antibody or a fragment thereof and a heavy chain of antibody or a fragment thereof, wherein the light chain of antibody or the fragment thereof comprises LCDR1, LCDR2 and LCDR3, and the heavy chain of antibody or the fragment thereof comprises HCDR1, HCDR2 and HCDR3, the LCDR1 comprises an amino acid sequence as shown in SEQ ID NO:1,
the LCDR2 comprises an amino acid sequence as shown in SEQ ID NO:2,
the LCDR3 comprises an amino acid sequence as shown in SEQ ID NO:3,
the HCDR1 comprises an amino acid sequence as shown in SEQ ID NO:4,
the HCDR2 comprises an amino acid sequence as shown in SEQ ID NO:5, and
the HCDR3 comprises an amino acid sequence as shown in SEQ ID NO:6.

2. The antibody or an antigen-binding fragment thereof according to claim 1, wherein the light chain of antibody or the fragment thereof comprises a light chain variable region VL, and the light chain variable region VL comprises an amino acid sequence as shown in SEQ ID NO:7; the antibody heavy chain or the fragment thereof comprises a heavy chain variable region VH, and the heavy chain variable region VH comprises an amino acid sequence as shown in SEQ ID NO:8.

3. The antibody or an antigen-binding fragment thereof according to claim 1, wherein the light chain of antibody comprises an amino acid sequence as shown in SEQ ID NO:11, and the heavy chain of antibody comprises an amino acid sequence as shown in SEQ ID NO:13.

4. The antibody or the antigen-binding fragment thereof according to claim 1, wherein the antibody is selected from the group comprising monoclonal antibody, single-strand antibody, chimeric antibody, and humanized antibody.

5. The antibody or the antigen-binding fragment thereof according to claim 1, wherein the antigen-binding fragment is selected from the group comprising Fab, Fab', F(ab)2, F(ab')2, Fv and ScFv fragments.

6. A pharmaceutical composition, comprising the antibody or the antigen-binding fragment thereof according to claim 1, and optionally a pharmaceutically acceptable adjuvant.

7. A method of inhibiting growth of CD38 positive tumor cells comprising contacting the CD38 positive tumor cells with the antibody or an antigen-binding fragment thereof according to claim 1.

* * * * *

SEQUENCE LISTING

<160> NUMBER OF SEQ ID NOS: 23

<210> SEQ ID NO 1
<211> LENGTH: 15
<212> TYPE: PRT
<213> ORGANISM: Artificial Sequence
<220> FEATURE:
<223> OTHER INFORMATION: LCDR1

```
<400> SEQUENCE: 1

Arg Ala Ser Ser Ser Val Ser Ser Ala Phe Ser Tyr Val His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: LCDR2

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: LCDR3

<400> SEQUENCE: 3

His His Ser Arg Glu Leu Pro Phe Thr
1               5

<210> SEQ ID NO 4
<211> LENGTH: 5
<212> TYPE: PRT
<213> ORGANISM: Artificial Sequence
<220> FEATURE:
<223> OTHER INFORMATION: HCDR1

<400> SEQUENCE: 4

Leu Tyr Trp Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: HCDR2

<400> SEQUENCE: 5

Lys Ile Asn Pro Asp Ser Ser Thr Ile Asn Tyr Thr Pro Ser Leu Lys
1               5                   10                  15

Asp

<210> SEQ ID NO 6
<211> LENGTH: 10
<212> TYPE: PRT
<213> ORGANISM: Artificial Sequence
<220> FEATURE:
<223> OTHER INFORMATION: HCDR3

<400> SEQUENCE: 6

Leu Trp Ile Ala Thr Gly Gly Phe Asp Tyr
1               5                   10

<210> SEQ ID NO 7
<211> LENGTH: 111
<212> TYPE: PRT
<213> ORGANISM: Artificial Sequence
<220> FEATURE:
<223> OTHER INFORMATION: VL
```

<400> SEQUENCE: 7

Glu Ile Val Met Thr Gln Ser Pro Ala Ser Leu Ser Ala Ser Leu Gly
1               5                   10                  15

Gln Arg Ala Thr Ile Ser Cys Arg Ala Ser Ser Val Ser Ser
            20                  25                  30

Ala Phe Ser Tyr Val His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Glu Leu Pro Phe Thr Phe Gly Ser Gly Thr Lys Leu Glu Ile Lys
            100                 105                 110

<210> SEQ ID NO 8
<211> LENGTH: 119
<212> TYPE: PRT
<213> ORGANISM: Artificial Sequence
<220> FEATURE:
<223> OTHER INFORMATION: VH

<400> SEQUENCE: 8

Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Asn Pro Asp Ser Ser Thr Ile Asn Tyr Thr Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Phe Asp Tyr Trp Gly Gln Gly
            100                 105                 110

Thr Thr Leu Thr Val Ser Ser
        115

<210> SEQ ID NO 9
<211> LENGTH: 333
<212> TYPE: DNA
<213> ORGANISM: Artificial Sequence
<220> FEATURE:
<223> OTHER INFORMATION: Codon optimized VL nucleotide

<400> SEQUENCE: 9
gagatcgtga tgacccagag ccctgccagc ctgagcgcca gcctgggcca gagggccacc      60
atcagctgca gggccagcag cagcgtgagc agcagcgcct tcagctacgt gcactggtac     120
cagcagaaga gcggccagcc tcctaagctg ctgatctacc tggccagcaa cctggagagc     180
ggcgtgcctg ccaggttcag cggcagcggc agcggcaccg acttcaccct gaccatccac     240
cctgtggaga gcgaggacgt ggccacctac tactgccacc acagcaggga gctgcctttc     300
accttcggca gcggcaccaa gctggagatc aag                                  333

<210> SEQ ID NO 10
<211> LENGTH: 357
<212> TYPE: DNA
<213> ORGANISM: Artificial Sequence
<220> FEATURE:
<223> OTHER INFORMATION: Codon optimized VH nucleotide

<400> SEQUENCE: 10

```
caggtgcagc tgctggagag cggcggcggc ctggtgcagc ctggcggcag cctgaagctg      60
agctgcgtgg ccagcggctt cgacttcagc ctgtactgga tgaactgggt gaggcaggcc     120
cctggcaagg cctggagtg atcggcaag atcaaccctg acagcagcac catcaactac      180
accctagcc tgaaggacaa gttcttcatc agcagggaca cgccaagaa caccctgtac      240
ctgcagatga ccaaggtgag gagcgaggac accgccctgt actactgcgc caggctgtgg     300
atcgccaccg gcggcttcga ctactgggc cagggcacca ccctgaccgt gagcagc        357
```

<210> SEQ ID NO 11
<211> LENGTH: 218
<212> TYPE: PRT
<213> ORGANISM: Artificial Sequence
<220> FEATURE:
<223> OTHER INFORMATION: SG003 light chain

<400> SEQUENCE: 11

```
Glu Ile Val Met Thr Gln Ser Pro Ala Ser Leu Ser Ala Ser Leu Gly
 1               5                  10                  15
Gln Arg Ala Thr Ile Ser Cys Arg Ala Ser Ser Val Ser Ser Ser
            20                  25                  30
Ala Phe Ser Tyr Val His Trp Tyr Gln Gln Lys Ser Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Gly Thr Asp Phe Thr Leu Thr Ile His
65                  70                  75                  80
Pro Val Glu Ser Glu Asp Val Ala Thr Tyr Tyr Cys His His Ser Arg
                85                  90                  95
Glu Leu Pro Phe Thr Phe Gly Ser Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 12
<211> LENGTH: 657
<212> TYPE: DNA

<213> ORGANISM: Artificial Sequence
<220> FEATURE:
<223> OTHER INFORMATION: SG003 light chain nucleotide

<400> SEQUENCE: 12

```
gagatcgtga tgacccagag ccctgccagc ctgagcgcca gcctgggcca gagggccacc      60
atcagctgca gggccagcag cagcgtgagc agcagcgcct tcagctacgt gcactggtac     120
cagcagaaga gcggccagcc tcctaagctg ctgatctacc tggccagcaa cctggagagc     180
ggcgtgcctg ccaggttcag cggcagcggc agcggcaccg acttcaccct gaccatccac     240
cctgtggaga gcgaggacgt ggccacctac tactgccacc acagcaggga gctgcctttc     300
accttcggca gcggcaccaa gctggagatc aagcgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga gtgttag        657
```

<210> SEQ ID NO 13
<211> LENGTH: 449
<212> TYPE: PRT
<213> ORGANISM: Artificial Sequence
<220> FEATURE:
<223> OTHER INFORMATION: SG003 heavy chain

<400> SEQUENCE: 13

```
Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Asn Pro Asp Ser Ser Thr Ile Asn Tyr Thr Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys
```

<210> SEQ ID NO 14
<211> LENGTH: 1350
<212> TYPE: DNA
<213> ORGANISM: Artificial Sequence
<220> FEATURE:
<223> OTHER INFORMATION: SG003 heavy chain nucleotide

<400> SEQUENCE: 14

```
caggtgcagc tgctggagag cggcggcggc ctggtgcagc ctggcggcag cctgaagctg    60
agctgcgtgg ccagcggctt cgacttcagc ctgtactgga tgaactgggt gaggcaggcc   120
cctggcaagg gcctggagtg gatcggcaag atcaaccctg acagcagcac catcaactac   180
accccctagcc tgaaggacaa gttcttcatc agcagggaca cgccaagaa cacccctgtac   240
ctgcagatga ccaaggtgag gagcgaggac accgccctgt actactgcgc caggctgtgg   300
atcgccaccg cggcttcga ctactgggc agggcacca ccctgaccgt gagcagcgct   360
agcaccaagg gcccatcggt cttccccctg gcaccctcct ccaagagcac ctctggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaagt tgagcccaaa   660
tcttgtgaca aaactcacac atgcccaccg tgcccagcac ctgaactcct gggggaccg    720
```

```
tcagtcttcc tcttcccccc aaaacccaag acaccctca tgatctcccg gaccccctgag      780
gtcacgtgcg tggtggtgga cgtgagccac gaagaccccg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggatgagctg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaatga                                      1350
```

<210> SEQ ID NO 15
<211> LENGTH: 30
<212> TYPE: PRT
<213> ORGANISM: Homo sapiens

<400> SEQUENCE: 15

```
Pro Glu Thr Val Leu Ala Arg Cys Val Lys Tyr Thr Glu Ile His Pro
1               5                   10                  15
Glu Met Arg His Val Asp Cys Gln Ser Val Trp Asp Ala Phe
            20                  25                  30
```

<210> SEQ ID NO 16
<211> LENGTH: 218
<212> TYPE: PRT
<213> ORGANISM: Artificial Sequence
<220> FEATURE:
<223> OTHER INFORMATION: Mutated light chain 1

<400> SEQUENCE: 16

```
Glu Ile Val Met Thr Gln Ser Pro Ala Ser Leu Ser Ala Ser Leu Gly
1               5                   10                  15
Gln Arg Ala Ser Ile Ser Cys Arg Ala Ser Asn Ser Val Ser Ser
            20                  25                  30
Ala Tyr Ser Tyr Val His Trp Tyr Gln Gln Lys Ser Gly Gln Pro Pro
        35                  40                  45
Lys Leu Leu Ile Tyr Leu Ala Ser Asn Ile Gln Ser Gly Val Pro Ala
    50                  55                  60
Arg Phe Ser Gly Ser Gly Ser Gly Thr Asp Phe Thr Leu Thr Ile His
65                  70                  75                  80
Pro Val Glu Ser Glu Asp Val Ala Thr Tyr Tyr Cys His His Ser Arg
                85                  90                  95
Gln Leu Pro Ser Thr Phe Gly Ser Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 17
<211> LENGTH: 449
<212> TYPE: PRT
<213> ORGANISM: Artificial Sequence
<220> FEATURE:
<223> OTHER INFORMATION: Mutated heavy chain 1

<400> SEQUENCE: 17

```
Gln Val Gln Leu Leu Glu Ser Gly Gly Gly Leu Val Gln Pro Gly Gly
1               5                   10                  15

Ser Leu Lys Leu Ser Cys Val Ala Ser Gly Tyr Asn Phe Ser Leu Tyr
            20                  25                  30

Tyr Met Asn Trp Val Arg Gln Ala Pro Gly Lys Gly Leu Glu Trp Ile
        35                  40                  45

Gly Lys Ile Gln Pro Glu Ser Ser Thr Ile Gln Tyr Thr Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Gly Ser Gly Gly Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 18
<211> LENGTH: 218
<212> TYPE: PRT
<213> ORGANISM: Artificial Sequence
<220> FEATURE:
<223> OTHER INFORMATION: Mutated light chain 2

<400> SEQUENCE: 18

Glu Ile Val Met Thr Gln Ser Pro Ala Ser Leu Ser Ala Ser Leu Gly
1               5                   10                  15

Gln Arg Ala Thr Ile Ser Cys Arg Ala Ser Ser Ser Val Ser Ser Ser
            20                  25                  30

Ala Tyr Ser Tyr Val His Trp Tyr Gln Gln Lys Ser Gly Gln Pro Pro
        35                  40                  45

Lys Leu Leu Ile Tyr Leu Ala Ser Asp Leu Gln Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Glu Leu Pro Tyr Ser Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 19
<211> LENGTH: 449
<212> TYPE: PRT
<213> ORGANISM: Artificial Sequence
<220> FEATURE:
<223> OTHER INFORMATION: Mutated heavy chain 2

<400> SEQUENCE: 19

```
Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Ser Pro Asn Ser Ser Thr Ile Asn Tyr Ser Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Tyr Ile Ala Ser Gly Gly Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
```

```
                   370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 20
<211> LENGTH: 218
<212> TYPE: PRT
<213> ORGANISM: Artificial Sequence
<220> FEATURE:
<223> OTHER INFORMATION: Mutated light chain 3

<400> SEQUENCE: 20

Glu Ile Val Met Thr Gln Ser Pro Ala Ser Leu Ser Ala Ser Leu Gly
1               5                   10                  15

Gln Arg Ala Thr Ile Ser Cys Arg Ala Ser Asn Ser Val Ser Thr Ser
                20                  25                  30

Ala Phe Ser Tyr Val His Trp Tyr Gln Gln Lys Ser Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Glu Val Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 449
<212> TYPE: PRT
<213> ORGANISM: Artificial Sequence
<220> FEATURE:
<223> OTHER INFORMATION: Mutated heavy chain 3

<400> SEQUENCE: 21

Gln Val Gln Leu Leu Glu Ser Gly Gly Gly Leu Val Gln Pro Gly Gly
```

-continued

```
1               5                   10                  15
Ser Leu Lys Leu Ser Cys Val Ala Ser Gly Phe Asp Phe Ser Leu Tyr
                20                  25                  30

Trp Met Asn Trp Val Arg Gln Ala Pro Gly Lys Gly Leu Glu Trp Ile
                35                  40                  45

Gly Lys Ile Ser Pro Asp Ser Ser Leu Asn Tyr Thr Pro Ser Val
        50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Tyr Asn Tyr Trp Gly Gln Gly
                100                 105                 110

Thr Thr Leu Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430
```

Ala Leu His Asn His Tyr Thr Gln Lys Ser Leu Ser Leu Ser Pro Gly
            435                 440                 445

Lys

<210> SEQ ID NO 22
<211> LENGTH: 218
<212> TYPE: PRT
<213> ORGANISM: Artificial Sequence
<220> FEATURE:
<223> OTHER INFORMATION: Light chain formula
<220> FEATURE:
<221> NAME/KEY: X20
<222> LOCATION: (20)..(20)
<223> OTHER INFORMATION: X20=T or S
<220> FEATURE:
<221> NAME/KEY: X27
<222> LOCATION: (27)..(27)
<223> OTHER INFORMATION: X27=S or N
<220> FEATURE:
<221> NAME/KEY: X31
<222> LOCATION: (31)..(31)
<223> OTHER INFORMATION: X31=S or T
<220> FEATURE:
<221> NAME/KEY: X34
<222> LOCATION: (34)..(34)
<223> OTHER INFORMATION: X34=F or Y
<220> FEATURE:
<221> NAME/KEY: X57
<222> LOCATION: (57)..(57)
<223> OTHER INFORMATION: X57=N or D
<220> FEATURE:
<221> NAME/KEY: X58
<222> LOCATION: (58)..(58)
<223> OTHER INFORMATION: X58=L or I
<220> FEATURE:
<221> NAME/KEY: X59
<222> LOCATION: (59)..(59)
<223> OTHER INFORMATION: X59=E or Q
<220> FEATURE:
<221> NAME/KEY: X97
<222> LOCATION: (97)..(97)
<223> OTHER INFORMATION: X97=E or Q
<220> FEATURE:
<221> NAME/KEY: X98
<222> LOCATION: (98)..(98)
<223> OTHER INFORMATION: X98=L or V
<220> FEATURE:
<221> NAME/KEY: X100
<222> LOCATION: (100)..(100)
<223> OTHER INFORMATION: X100=F or S
<220> FEATURE:
<221> NAME/KEY: X101
<222> LOCATION: (101)..(101)
<223> OTHER INFORMATION: X101=T or S

<400> SEQUENCE: 22

Glu Ile Val Met Thr Gln Ser Pro Ala Ser Leu Ser Ala Ser Leu Gly
1               5                   10                  15

Gln Arg Ala Xaa Ile Ser Cys Arg Ala Ser Xaa Ser Val Ser Xaa Ser
            20                  25                  30

Ala Xaa Ser Tyr Val His Trp Tyr Gln Gln Lys Ser Gly Gln Pro Pro
        35                  40                  45

Lys Leu Leu Ile Tyr Leu Ala Ser Xaa Xaa Xaa Ser Gly Val Pro Ala
50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Xaa Xaa Pro Xaa Xaa Phe Gly Ser Gly Thr Lys Leu Glu Ile Lys Arg

```
                100             105             110
Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 23
<211> LENGTH: 449
<212> TYPE: PRT
<213> ORGANISM: Artificial Sequence
<220> FEATURE:
<223> OTHER INFORMATION: Heavy chain formula
<220> FEATURE:
<221> NAME/KEY: X27
<222> LOCATION: (27)..(27)
<223> OTHER INFORMATION: X27=F or Y
<220> FEATURE:
<221> NAME/KEY: X28
<222> LOCATION: (28)..(28)
<223> OTHER INFORMATION: X28=D or N
<220> FEATURE:
<221> NAME/KEY: X33
<222> LOCATION: (33)..(33)
<223> OTHER INFORMATION: X33=W or Y
<220> FEATURE:
<221> NAME/KEY: X52
<222> LOCATION: (52)..(52)
<223> OTHER INFORMATION: X52=N, Q or S
<220> FEATURE:
<221> NAME/KEY: X54
<222> LOCATION: (54)..(54)
<223> OTHER INFORMATION: X54=D, E or N
<220> FEATURE:
<221> NAME/KEY: X57
<222> LOCATION: (57)..(57)
<223> OTHER INFORMATION: 57=T or S
<220> FEATURE:
<221> NAME/KEY: X58
<222> LOCATION: (58)..(58)
<223> OTHER INFORMATION: X58=I or L
<220> FEATURE:
<221> NAME/KEY: X59
<222> LOCATION: (59)..(59)
<223> OTHER INFORMATION: X59=N or Q
<220> FEATURE:
<221> NAME/KEY: X61
<222> LOCATION: (61)..(61)
<223> OTHER INFORMATION: X61=T or S
<220> FEATURE:
<221> NAME/KEY: X64
<222> LOCATION: (64)..(64)
<223> OTHER INFORMATION: X64=L or V
<220> FEATURE:
<221> NAME/KEY: X100
<222> LOCATION: (100)..(100)
<223> OTHER INFORMATION: X100=W or Y
<220> FEATURE:
<221> NAME/KEY: X102
<222> LOCATION: (102)..(102)
<223> OTHER INFORMATION: X102=A or G
<220> FEATURE:
```

```
<221> NAME/KEY: X103
<222> LOCATION: (103)..(103)
<223> OTHER INFORMATION: X103=T or S
<220> FEATURE:
<221> NAME/KEY: X106
<222> LOCATION: (106)..(106)
<223> OTHER INFORMATION: X106=F or Y
<220> FEATURE:
<221> NAME/KEY: X107
<222> LOCATION: (107)..(107)
<223> OTHER INFORMATION: X107=D or N

<400> SEQUENCE: 23
```

Gln Val Gln Leu Leu Glu Ser Gly Gly Gly Leu Val Gln Pro Gly Gly
1               5                   10                  15

Ser Leu Lys Leu Ser Cys Val Ala Ser Gly Xaa Xaa Phe Ser Leu Tyr
            20                  25                  30

Xaa Met Asn Trp Val Arg Gln Ala Pro Gly Lys Gly Leu Glu Trp Ile
        35                  40                  45

Gly Lys Ile Xaa Pro Xaa Ser Ser Xaa Xaa Xaa Tyr Xaa Pro Ser Xaa
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Xaa Ile Xaa Xaa Gly Gly Xaa Xaa Tyr Trp Gly Gln Gly
            100                 105                 110

Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```